United States Patent
Pappone et al.

(10) Patent No.: US 11,844,614 B2
(45) Date of Patent: *Dec. 19, 2023

(54) ANALYZING AND MAPPING ECG SIGNALS AND DETERMINING ABLATION POINTS TO ELIMINATE BRUGADA SYNDROME

(71) Applicants: BIOSENSE WEBSTER (ISRAEL) LTD., Yokneam (IL); Carlo Pappone, Cernusco Lombardone (IT)

(72) Inventors: Carlo Pappone, Cernusco Lombardone (IT); Aharon Turgeman, Zichron Yaacov (IL); Paolo Roberto Pozzi, Limbiate (IT); Andrea Natalizia, Rome (IT)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 376 days.

This patent is subject to a terminal disclaimer.

(21) Appl. No.: 17/148,032

(22) Filed: Jan. 13, 2021

(65) Prior Publication Data
US 2021/0128043 A1  May 6, 2021

Related U.S. Application Data

(63) Continuation of application No. 15/854,485, filed on Dec. 26, 2017, now Pat. No. 10,893,819.
(Continued)

(51) Int. Cl.
*A61B 18/12* (2006.01)
*A61B 5/283* (2021.01)
(Continued)

(52) U.S. Cl.
CPC .............. *A61B 5/283* (2021.01); *A61B 5/316* (2021.01); *A61B 5/366* (2021.01); *A61B 5/6852* (2013.01);
(Continued)

(58) Field of Classification Search
CPC ................ A61B 18/1492; A61B 34/10; A61B 2018/00642; A61B 2018/00702;
(Continued)

(56) References Cited

U.S. PATENT DOCUMENTS

| | | | |
|---|---|---|---|
| 5,391,199 | A | 2/1995 | Ben-Haim |
| 5,443,489 | A | 8/1995 | Ben-Haim |

(Continued)

FOREIGN PATENT DOCUMENTS

| | | |
|---|---|---|
| EP | 2901953 A1 | 8/2015 |
| WO | 03/011112 A2 | 2/2003 |

(Continued)

OTHER PUBLICATIONS

Koonlawee Nademanee, "Prevention of Ventricular Fibrillation Episodes in Brugada Syndrome by Catheter Ablation Over the Anterior Right Ventricular Outflow Tract Epicardium Clinical Perspective", Circulation, vol. 123, No. 12, Mar. 29, 2011, pp. 1270-1279.

(Continued)

*Primary Examiner* — Daniel W Fowler
(74) *Attorney, Agent, or Firm* — Volpe Koenig

(57) ABSTRACT

A system and method for Brugada syndrome epicardial ablation comprising preparing an endocardial duration map; preparing a baseline epicardial duration map comprising at least one or more areas of delimitation; and when some of the areas of delimitation are greater than 200 ms, performing epicardial ablation of the areas of delimitation greater than 200 ms. The method may further comprise preparing an updated epicardial duration map after performing epicardial ablation, and determining whether or not a BrS pattern appears in the updated epicardial duration map; and when the BrS pattern appears, performing epicardial ablation. The method may further comprise preparing an updated epicar- (Continued)

dial duration map after performing epicardial ablation, and determining whether or not an abnormal EGM exists in the updated epicardial duration map; and when the abnormal EGM exists, performing epicardial ablation. The method may further comprise preparing an updated epicardial map comprising maintaining anatomical volume data and adding electroanatomical data.

34 Claims, 22 Drawing Sheets

Related U.S. Application Data

(60) Provisional application No. 62/450,388, filed on Jan. 25, 2017.

(51) Int. Cl.
| | |
|---|---|
| *A61B 5/00* | (2006.01) |
| *A61B 18/14* | (2006.01) |
| *A61B 34/10* | (2016.01) |
| *A61B 5/316* | (2021.01) |
| *A61B 5/366* | (2021.01) |
| *A61B 34/20* | (2016.01) |
| *A61B 18/00* | (2006.01) |
| *A61B 17/00* | (2006.01) |
| *A61B 5/352* | (2021.01) |
| *A61B 5/361* | (2021.01) |

(52) U.S. Cl.
CPC .......... *A61B 18/1492* (2013.01); *A61B 34/10* (2016.02); *A61B 5/352* (2021.01); *A61B 5/361* (2021.01); *A61B 2017/00053* (2013.01); *A61B 2018/00642* (2013.01); *A61B 2018/00702* (2013.01); *A61B 2018/00839* (2013.01); *A61B 2034/2046* (2016.02); *A61B 2034/2051* (2016.02); *A61B 2034/2072* (2016.02)

(58) Field of Classification Search
CPC .. A61B 2018/00839; A61B 2034/2046; A61B 2034/2051; A61B 2034/2072
See application file for complete search history.

(56) References Cited

U.S. PATENT DOCUMENTS

| | | | |
|---|---|---|---|
| 5,558,091 A | 9/1996 | Acker et al. | |
| 5,944,022 A | 8/1999 | Nardella et al. | |
| 5,983,126 A | 11/1999 | Wittkampf | |
| 6,172,499 B1 | 1/2001 | Ashe | |
| 6,177,792 B1 | 1/2001 | Govari et al. | |
| 6,266,551 B1 | 7/2001 | Osadchy et al. | |
| 6,456,828 B1 | 9/2002 | Ozluturk | |
| 6,633,773 B1 | 10/2003 | Reisfeld | |
| 6,690,963 B2 | 2/2004 | Ben-Haim et al. | |
| 6,694,178 B1 | 2/2004 | Soula et al. | |
| 6,788,967 B2 | 9/2004 | Ben-Haim et al. | |
| 8,010,186 B1 | 8/2011 | Ryu | |
| 10,888,379 B2 | 1/2021 | Pappone et al. | |
| 2004/0059237 A1 | 3/2004 | Narayan et al. | |
| 2005/0010201 A1 | 1/2005 | Abboud et al. | |
| 2005/0177049 A1 | 8/2005 | Hardahl et al. | |
| 2006/0058693 A1 | 3/2006 | Beatty et al. | |
| 2007/0073177 A1 | 3/2007 | Kontothanassis et al. | |
| 2007/0167801 A1* | 7/2007 | Webler .................... G06T 19/00 600/459 |
| 2007/0197929 A1* | 8/2007 | Porath .................... A61B 5/349 600/509 |
| 2007/0244402 A1 | 10/2007 | Brockway et al. | |
| 2008/0009758 A1 | 1/2008 | Voth | |
| 2008/0058657 A1* | 3/2008 | Schwartz .............. A61B 5/6805 600/508 |
| 2008/0118438 A1* | 5/2008 | Antzelevitch ...... G01N 33/6893 530/387.9 |
| 2008/0214457 A1* | 9/2008 | Deschenes ........... C07K 14/705 530/324 |
| 2009/0093806 A1 | 4/2009 | Govari et al. | |
| 2009/0099468 A1 | 4/2009 | Thiagalingam et al. | |
| 2009/0137916 A1 | 5/2009 | Maison-Blanche et al. | |
| 2009/0138007 A1 | 5/2009 | Govari et al. | |
| 2013/0116681 A1 | 5/2013 | Zhang | |
| 2013/0338518 A1 | 12/2013 | Zoica | |
| 2014/0081262 A1 | 3/2014 | Koblish et al. | |
| 2015/0238102 A1 | 8/2015 | Rubinstein et al. | |
| 2016/0073960 A1 | 3/2016 | Jung et al. | |
| 2016/0296141 A1 | 10/2016 | Rodiera Olive et al. | |

FOREIGN PATENT DOCUMENTS

| | | |
|---|---|---|
| WO | 2006/066324 A1 | 6/2006 |
| WO | 2013123549 A1 | 2/2013 |
| WO | 2016/123390 A1 | 8/2016 |

OTHER PUBLICATIONS

Circ Arrhythm Electrophysiol. May 2017;10(5):e005053. doi: 10.1161/CIRCEP.117.005053.

European Search Report for Application No. 18153220.1 dated Jun. 7, 2018.

Zhang et al., "Characterization of the epicardial substrate for catheter ablation of Brugada syndrome," Heart Rhythm, 2016, pp. 2151-2158, vol. 13, No. 11.

Munoz et al., Teaching Points With 3-Dimensional Mapping of Cardiac Arrhythmias, Circ Arrhythm Electrophysiol., 2011, 4:e22-e25.

Extended European Search Report dated May 30, 2018 for the European Patent Application No. 18153252.4.

\* cited by examiner

Electrophysiological characteristics of study population according to the clinical presentation

| Characteristics | Group 1 | | *Group 2 (N=72) | P-Value* |
|---|---|---|---|---|
| | *Worst (N=39) | *Not worst (N=24) | | |
| Baseline abnormal area, cm² | | | | 0.013 |
| Median | 8.0 | 7.0 | 4.6 | a vs b P=0.234 |
| IQR | 5.4-12.3 | 3.6-11.4 | 2.5-9.4 | a vs c P=0.004 |
| Min-Max | 0.5-56.6 | 0-23.9 | 0-17.4 | b vs c P=0.229 |
| Abnormal area after ajmaline, cm² | | | | |
| >200 ms | | | | 0.001 |
| Median | 20.0 | 19.2 | 15.7 | a vs b P=0.692 |
| IQR | 17.9-22.4 | 14.4-28.1 | 13.0-19.1 | a vs c P<0.001 |
| Min-Max | 9.3-64.2 | 11.9-36.6 | 5-51 | b vs c P=0.033 |
| >250 ms | | | | 0.004 |
| Median | 10.0 | 9.2 | 7.3 | a vs b P=0.353 |
| IQR | 7.2-11.5 | 5.6-11.9 | 5.2-9.1 | a vs c P=0.001 |
| Min-Max | 4.5-35.0 | 2.5-16.0 | 1-23.5 | b vs c P=0.143 |
| >280 ms | | | | <0.001 |
| Median | 6.5 | 5.2 | 4.8 | a vs b P=0.357 |
| IQR | 4.7-7.3 | 4.3-7.2 | 2.9-5.6 | a vs c P<0.001 |
| Min-Max | 1.9-22.1 | 0.6-12.3 | 0.4-12.5 | b vs c P=0.028 |
| Baseline potential duration, ms | | | | 0.003 |
| Median | 230 | 185 | 177 | a vs b P=0.031 |
| IQR | 192-234 | 157-227 | 150-226 | a vs c P=0.001 |
| Min-Max | 129-310 | 124-310 | 123-325 | b vs c P=0.408 |
| Potential duration after ajmaline, ms | | | | 0.005 |
| Median | 330 | 310 | 300 | a vs b P=0.061 |
| IQR | 310-333 | 280-330 | 260-330 | a vs c P=0.001 |
| Min-Max | 219-423 | 226-405 | 219-480 | b vs c P=0.372 |
| Baseline local activation time, ms | | | | 0.132 |
| Median | 72 | 66 | 73 | |
| IQR | 64-76 | 62-76 | 64-81 | |
| Min-Max | 59-84 | 53-83 | 53-89 | |
| Local activation time after ajmaline, ms | | | | 0.126 |
| Median | 82 | 78 | 85 | |
| IQR | 78-89 | 74-89 | 77-94 | |
| Min-Max | 70-96 | 68-95 | 68-103 | |
| Baseline low-voltage area, cm² | | | | <0.001 |
| Median | 1 | 0 | 0 | a vs b P=<0.001 |
| IQR | 0-7 | 0-0 | 0-0 | a vs c P=<0.001 |
| Min-Max | 0-13 | 0-1 | 0-2 | b vs c P=0.614 |
| Low-voltage area after ajmaline, cm² | | | | <0-001 |
| Median | 2 | 0 | 0 | a vs b P=<0.001 |
| IQR | 0-12 | 1-0 | 0-0 | a vs c P=<0.001 |
| Min-Max | 0-21 | 0-2 | 0-4 | b vs c P=0.392 |

*By Kruskal-Wallis H Test with Dunn's test for multiple comparisons

FIGURE 16

Clinical Characteristics of the Study Patients according to clinical presentation

| Characteristics | Group 1 | | Group 2 (N=72) | P-Value |
|---|---|---|---|---|
| | Worst (N=39) | Not worst (N=24) | | |
| Male sex – no. (%) | 29 (74.4) | 18 (75.0) | 59 (81.9) | 0.584 |
| Age – yr | | | | 0.974* |
|   Mean±SD | 39-9±11.4 | 39-3±9.7 | 39.6±11.7 | |
|   Min-Max | 22-63 | 21-59 | 18-71 | |
| BrS-ECG pattern – no. (%) | | | | 0.833 |
|   Type 1 | 8 (20.5) | 7 (29.2) | 16 (22.2) | |
|   Type 2 | 15 (38.5) | 7 (25.0) | 26 (36.1) | |
|   Type 3 | 16 (41.0) | 11 (45.8) | 30 (41.7) | |
| Family history of SD – no. (%) | 6 (15.4) | 6 (25.0) | 15 (20.8) | 0.630 |
| Probands – no. (%) | 9 (23.1) | 5 (20.8) | 8 (11.1) | 0.213 |
| Relatives – no. (%) | 4 (10.3) | 2 (8.3) | 12 (16.7) | 0.465 |
| Positive SCN5A – no. (%) | 12 (30.8) | 7 (29.2) | 13 (18.1) | 0.254 |
| Pre-RFA ICD therapy – no. (%) | 27 (69.2) | 4 (16.7) | 1 (1.4) | <0.001 |
| Post-RFA ICD therapy – no. (%) | 2 (5.1) | 0 (0) | 0 (0) | 0.112 |
| Follow-up – months | | | | 0.188† |
|   Median | 10 | 12 | 9 | |
|   IQR | 7-12 | 8-12 | 7-11.8 | |
|   Min-Max | 3-13 | 5-13 | 3-13 | |

\* By one-way ANOVA
↑By Kruskal-Wallis H Test

FIGURE 17

ANALYZING AND MAPPING ECG SIGNALS AND DETERMINING ABLATION POINTS TO ELIMINATE BRUGADA SYNDROME

CROSS REFERENCE TO RELATED APPLICATION

This application incorporates by reference as if fully set forth U.S. patent application Ser. No. 15/854,492, filed Dec. 26, 2017, titled "A Method And System For Eliminating A Broad Range Of Cardiac Conditions By Analyzing Intracardiac Signals, Providing A Detailed Map And Determining Potential Ablation Points." This application is a continuation of U.S. application Ser. No. 15/854,485, filed on Dec. 26, 2017, which claims the benefit of U.S. Provisional Application No. 62/450,388, filed on Jan. 25, 2017, which are incorporated by reference as if fully set forth.

SUMMARY

There is provided according to embodiments of a system and method that enables improved analysis of electrocardiography (ECG) signals to eliminate Brugada syndrome. (BrS) The system and method can create a potential duration map (PDM) by automatically measuring duration of signals and annotating ventricular eletrogram (EGM) duration from onset to offset.

The method of Brugada syndrome epicardial ablation may comprise preparing an endocardial duration map, preparing a baseline epicardial duration map comprising at least one or more areas of delimination, and when some of the areas of delimination are greater than 200 ms, performing epicardial ablation of the areas of delimination greater than 200 ms. The method may further comprise preparing an updated epicardial duration map after performing epicardial ablation, and determining whether or not a BrS pattern appears in the updated epicardial duration map; and when the BrS pattern appears, performing epicardial ablation. The method may further comprise preparing an updated epicardial duration map after performing epicardial ablation, and determining whether or not an abnormal EGM exists in the updated epicardial duration map; and when the abnormal EGM exists, performing epicardial ablation. The method may further comprise preparing an updated epicardial map comprising maintaining anatomical volume data and adding electroanatomical data. The method may further comprise the baseline epicardial duration map, and the updated epicardial map displaying concentric areas having cut-off intervals. The method may further comprise, in the step of preparing a baseline epicardial duration map, defining a window of interest (WOI) comprising at least a cycle length, calculating previous heart beats based on the cycle length and reference annotation, assigning the heart beats within the cycle length of the WOI to the WOI, finding a start potential duration and an end potential duration, and selecting an ablation point based on a heart beat having a minimum standard deviation from the heart beats assigned to the WOI.

The system for Brugada syndrome epicardial ablation in a heart may comprise a catheter for measuring ECG signals, a computer adapted to: prepare an endocardial duration map; prepare a baseline epicardial duration map comprising at least one or more areas of delimination; and when one or more of the areas of delimination are greater than 200 ms, performing epicardial ablation of the areas of delimination greater than 200 ms; and a display device for displaying the endocardial duration map and the baseline epicardial map. The computer in the system may further be adapted to prepare an updated epicardial duration map after performing epicardial ablation, and determine whether or not a BrS pattern appears in the updated epicardial duration map, and when the BrS pattern appears, perform epicardial ablation. The computer in the system may further be adapted to prepare an updated epicardial duration map after performing epicardial ablation, and determine whether or not an abnormal EGM exists in the updated epicardial duration map, and when the abnormal EGM exists, perform epicardial ablation. The system may further comprise a tool for injecting ajmaline into the heart. The computer in the system may further be adapted to prepare an updated epicardial map after performing epicardial ablation, comprising maintaining anatomical volume data and adding electroanatomical data. The computer in the system may further be adapted to display concentric areas having cut-off intervals on the baseline epicardial duration map and the updated epicardial map. The computer in the system may further be adapted to prepare the baseline epicardial duration map by performing steps of defining a WOI comprising at least a cycle length, calculating previous heart beats based on the cycle length and reference annotation, assigning the heart beats within the cycle length of the WOI to the WOI, finding a start potential duration and an end potential duration, and selecting an ablation point based on a heart beat having a minimum standard deviation from the heart beats assigned to the WOI.

A computer program product for Brugada syndrome epicardial ablation is also presented.

These and other objects, features and advantages of the present invention will be apparent from the following detailed description of illustrative embodiments thereof, which is to be read in connection with the accompanying drawings.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals.

FIG. 16 shows a table of ablation results for the example patient.

FIG. 17 shows a table of electrophysiological characteristics of study population.

DETAILED DESCRIPTION OF THE INVENTION

Brugada syndrome (BrS) is an ECG abnormality with a high incidence of sudden death in patients with structurally normal hearts. This syndrome or disorder is characterized by sudden death associated with one of several ECG patterns characterized by incomplete right bundle-branch block and ST-segment elevations in the anterior precordial leads.

BrS is a genetically determined disease predisposing to sudden cardiac death due to ventricular malignant arrhythmias. A first aspect of the present system and method is treating Brugada syndrome by analyzing the EGM signals, determining the ablation points, and manually editing the calipers on the mapping catheter to set the duration. A second aspect of the present system is an example method, presented below, which enables visualization of the abnormal substrate according to the EGMs' duration found on the epicardial layer of BrS patients.

Figure 1:
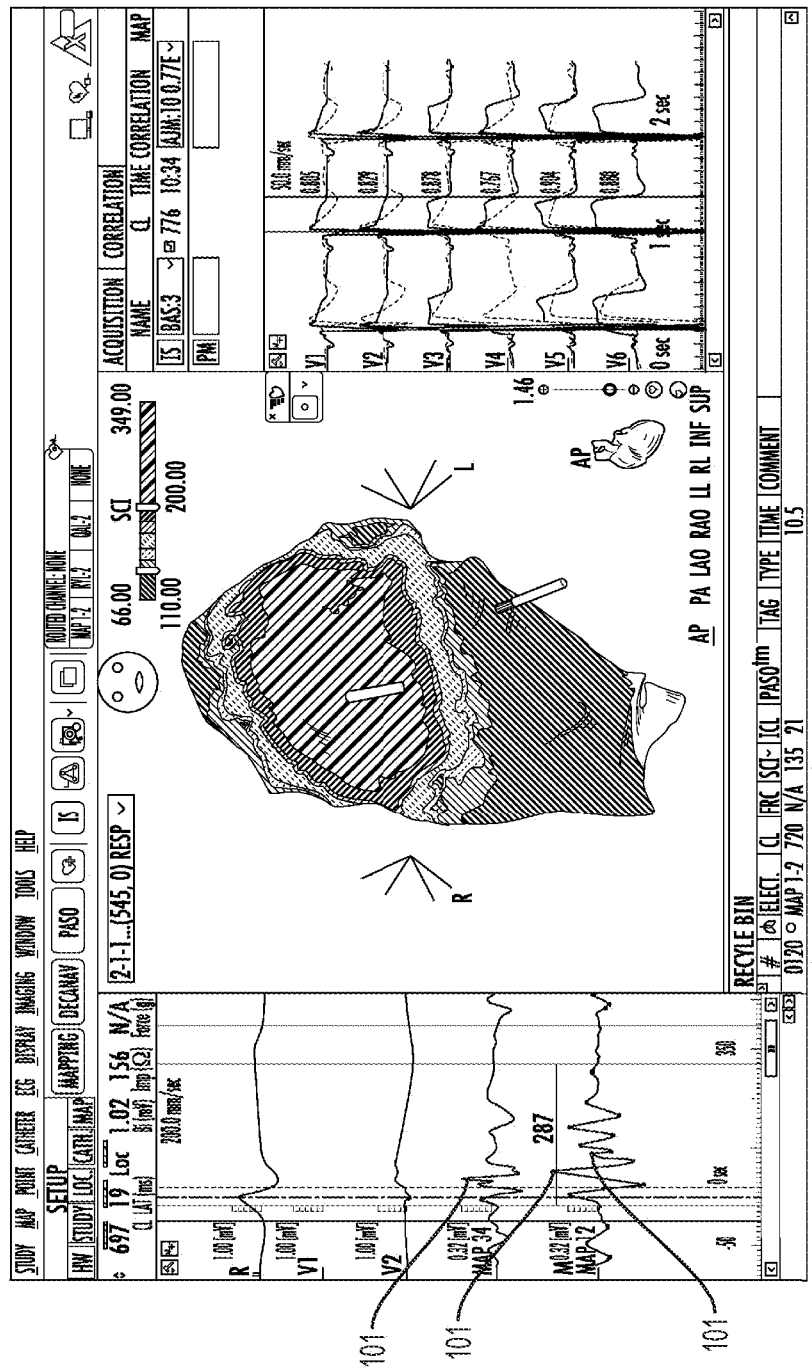
FIG. 1 shows a Potential Duration Map (PDM).

FIG. 1 shows a Potential Duration Map (PDM) (e.g., RV epicarial Map), in the center, a selected point viewer in the left column, and Paso viewer in the right column. The PDM uses a scale of Shortex Complex Interval (SCI) which ranges from 15.0 ms to 171.0 ms. The PDM is created using the present system to measure the Potential Duration for each point that the EGM automatically creates in accordance with the mapping method. The EGM shown in FIG. 1, left side, includes MAP1-2 and MAP3-4, each having peaks 101 that indicate changes in direction of the tracings of the mapping catheter.

The example method is performed to visualize the abnormal substrate according to the EGMs duration found on the epicardial layer of BrS patients. Using, for example, the Complex Fractionated Atrial Electrograms (CFAE) module of the CARTO® 3 system (Biosense Webster), for each electroanatomical acquired point, two calipers are manually moved by placing the first on the onset and the second on the offset of the EGM recorded. Note that CFAE performs calculations using the fragmentation in Bipolar EGM signal in the acquired point. The fragmentation is marked as interval duration with left and right borders. The present method results in the exact measurement of the ventricular EGM duration, enabling the creation of a PDM that may comprise a coded mapping, such as a color-coded map (color shown using different hatching patterns), showing different degrees of prolongation. The appropriate characterization of the abnormal substrate along with the localization of such EGMs helps to establish the appropriate target for catheter ablation in order to achieve a successful procedure, and the PDM enables such characterization.

As shown in FIG. 1, the present system can be used to automatically annotate and measure EGM signals (as shown in the left panel) to create the PDM for Brugada syndrome elimination by ablation. This system uses an annotation technique to improve conventional software, such as CARTO® 3, by automating the process of detecting where to ablate.

Figure 2:
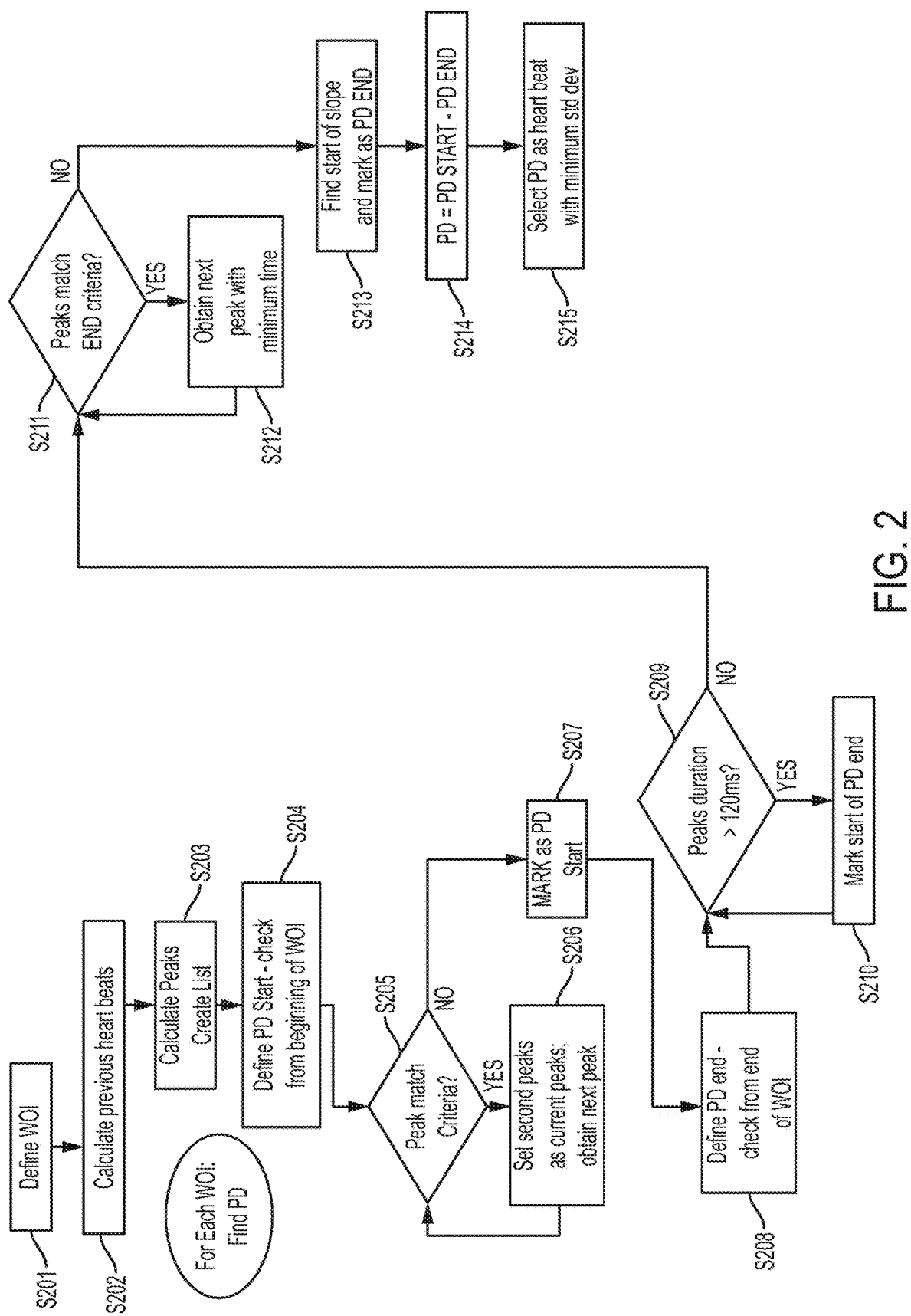
FIG. 2 is a flow diagram of an example method in an embodiment.

FIG. 2 is a flow diagram of an example method for automatically determining ablation points in Brugada syndrome is presented. As shown in FIG. 2, the method is performed as follows.

In step S201, a Window Of Interest (WOI) is defined, the WOI being the interval in the EGM and/or ECG which is normally used to calculate the voltage amplitude (peak to peak mV) and the signal duration. An example EGM is shown in FIG. 1.

In step S202, at least two previous heart beats are calculated based on cycle length and reference annotation, and a WOI is assigned for two of the heart beats. Note that each electroanatomical acquired point (e.g., point EGM) contains data to be used for coloring the Map according to Map Type, such as PDM, CFAE, LAT, Bipolar Voltage etc. Example maps are shown in FIGS. 10-14, (described hereinafter). In one acquired point, for example, a window equal to 2500 ms of ECG and EGM is recorded. For example, if the reference annotation for a heart beat lays at 2000 ms, the first WOI [−50 ms, 350 ms] goes from 2000 ms−50 ms (e.g., 1950 ms) to 2000 ms+350 ms (e.g., 2350 ms). If the heart beat cycle length is 800 ms, there is more than one heart beat in the 2500 ms WOI. The previous heart beat reference lays at 1200 ms (2000 ms−800 ms [e.g., 1200 ms]) and the WOI will be from 1200 ms−50 ms (e.g., 1150 ms) to 1200 ms+350 ms (e.g., 1550 ms). It should be noted that the abovementioned time intervals have been used by way of example and should not be considered as limiting.

Next, for each WOI of each heart beat, the Potential Duration is calculated as shown in steps S203-211, as follows.

In step S203, the peaks are calculated based on a predetermined threshold in WOI and a list of peaks in WOI are created. The EGM signal values are measured in mV, and, in one example, a peak with mV value greater than 0.05 mV is marked. However, it should be noted that the peak threshold may be set by the physician.

In step S204, Potential Duration Start (PD-Start) is defined by checking from the beginning of the WOI, as shown in steps S205-S207 as follows.

In step S205, it is determined whether or not two consecutive peaks have the same sign and the same peaks absolute values are less than 2*Min.

In step S206, if S205=YES (two consecutive peaks have the same sign and the absolute value of the consecutive peaks is less than 2*Min), the current peak is set as the second peak, the next peak is obtained and the method returns to step S205.

In step S207, if S205=NO (two consecutive peaks do not have the same sign and/or the absolute value of the consecutive peaks is greater than or equal to 2*Min), the start of the slope before the current peak is found and marked it as Start potential duration.

In step S208, Potential Duration End (PD-END) is defined, checking from the ending of the WOI, as shown in steps S209-S210 as follows.

In step S209, it is determined whether or not two consecutive peaks' distance is greater than 120 ms.

In step S210, if S209=YES (two consecutive peaks are greater than 120 ms), the start of PD-End portion is marked as the peak with minimum time of the two consecutive peaks and the method returns to step S209.

In step S211, if S209=NO (two consecutive peaks do not have distance greater than 120 ms), then in step S211, it is determined whether two consecutive peaks have the same sign and the peaks' absolute values are less than 2*Min Threshold, whether the time between two consecutive peaks is greater than 120 ms or whether the time between two consecutive peaks is less than 25 ms.

Keeping in mind that the stability and reproducibility of the duration of the potential can be a crucial factor, in one embodiment, the present technique can consider another factor; the technique can verify, in the presence of a double or late potential, that the late activity is also present in all the beats included in the 2500 ms recording window.

In step S212, if S211=YES (two consecutive peaks have the same sign and the peaks' absolute values are less than 2*Min, the time between two consecutive peaks is greater than 120 ms or the time between two consecutive peaks is less than 25 ms), the next peak is obtained with minimum time, and the method returns to step S211.

In step S213, if S211=NO (two consecutive peaks do not have the same sign, the peaks absolute values are equal to or greater than 2*Min or the time between two consecutive peaks is less than or equal to than 120 ms or the time between two consecutive peaks is greater than or equal to 25 ms), the start of the slope after the current peak is found and marked as End Potential Duration.

In step S214, the Potential Duration value is calculated as the difference between potential duration Start and potential duration End in ms.

In step S215, the selected point potential duration value is set as the heart beat which has the minimum standard deviation of the positions on each heart beat WOI. Note that the area measurement between the BS ECG IS when inducing the BrS and the BS ECG IS after treating the BrS can provide the indication of when to stop the procedure.

In accordance with the PDM and the analysis described above, any EGM showing a duration ≥200 ms may be considered abnormal, and thus represents a target for catheter ablation. Three different concentric areas are identified according to the degree of prolongation by setting different cut-off intervals, for example, ≥300 ms, ≥250 ms and ≥200 ms, respectively. The different cut-offs are necessary to guide the ablation procedure, starting from the small "core" of the substrate (area showing EGM duration ≥300 ms) and subsequently moving to the larger regions having potential duration ≥250 ms and ≥200 ms, respectively, as shown in FIGS. 3A, 3B and 3C, described in more detail below.

The inventive technique may enable the elimination of all delayed and prolonged EGM activities located in the above-mentioned regions. Class IC drug challenge is performed at the end of ablation in order to ensure successful abolition of all abnormal potentials and stable BrS-ECG pattern elimination. In cases of BrS-ECG pattern reappearance after drug challenge, the epicardial PDM is a remap of the epicardial using PDM to identify target locations with PDM bigger than 200 ms for ablation. This is repeated to identify any residual or additional abnormal signals for further RF applications in order to completely normalize the ECG pattern. The final end-point, e.g., ablation point, is obtained by the elimination and the non-inducibility of the BrS ECG pattern proved by the Class IC drug test and the abolition, using RF catheter ablation, of any prolonged and fragmented potential identified during the mapping procedure.

Figure 3A:
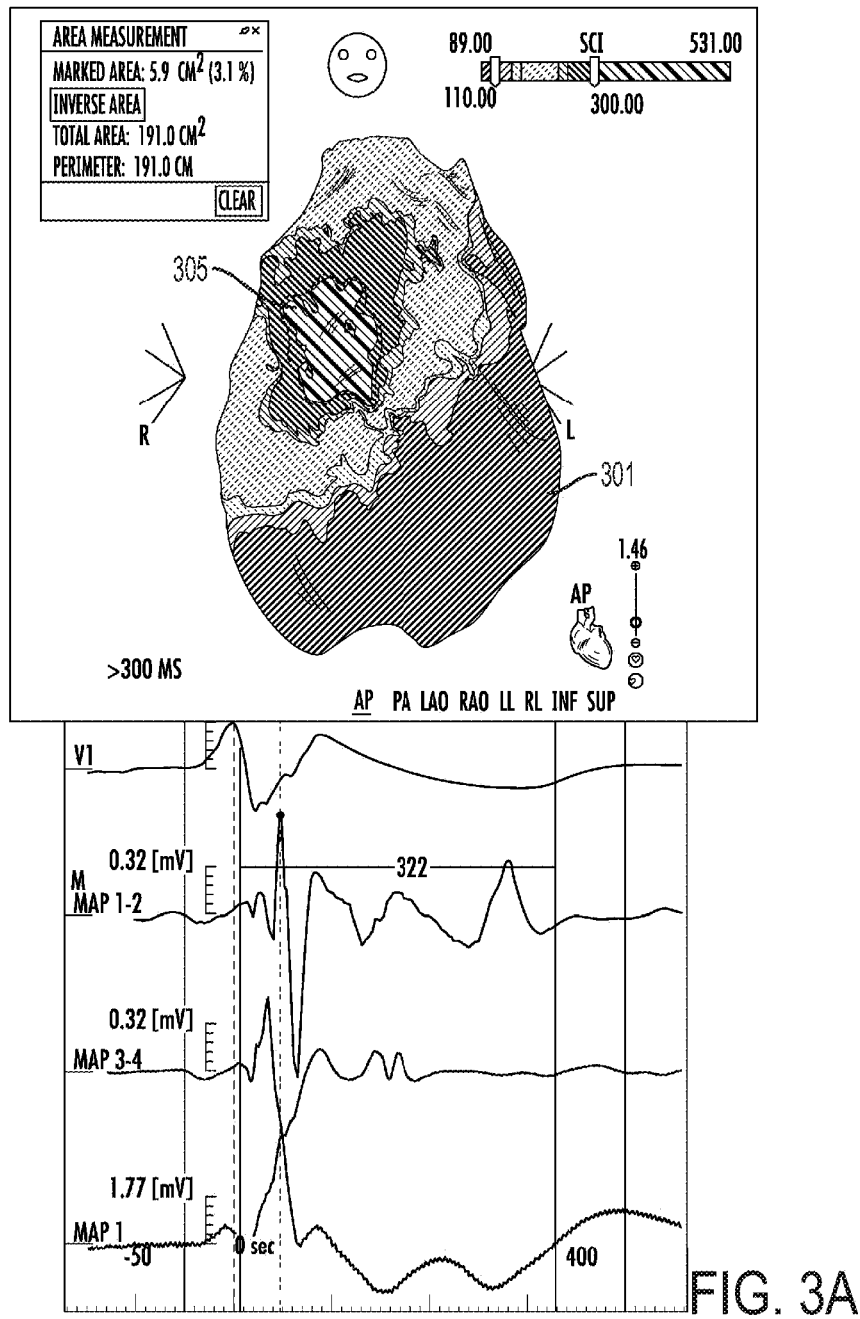
FIGS. 3A, 3B, 3C show Brugada syndrome concentric substrate distribution.
Figure 3B:
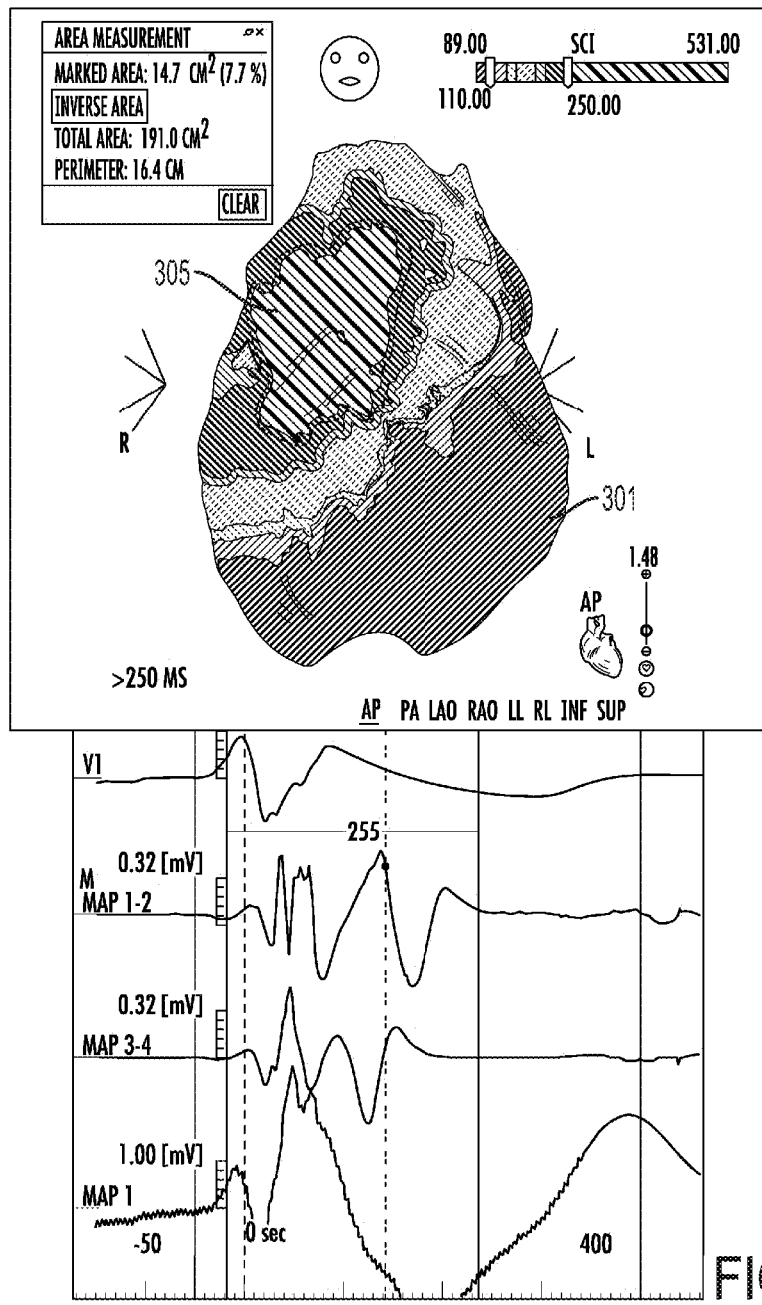
Figure 3C:
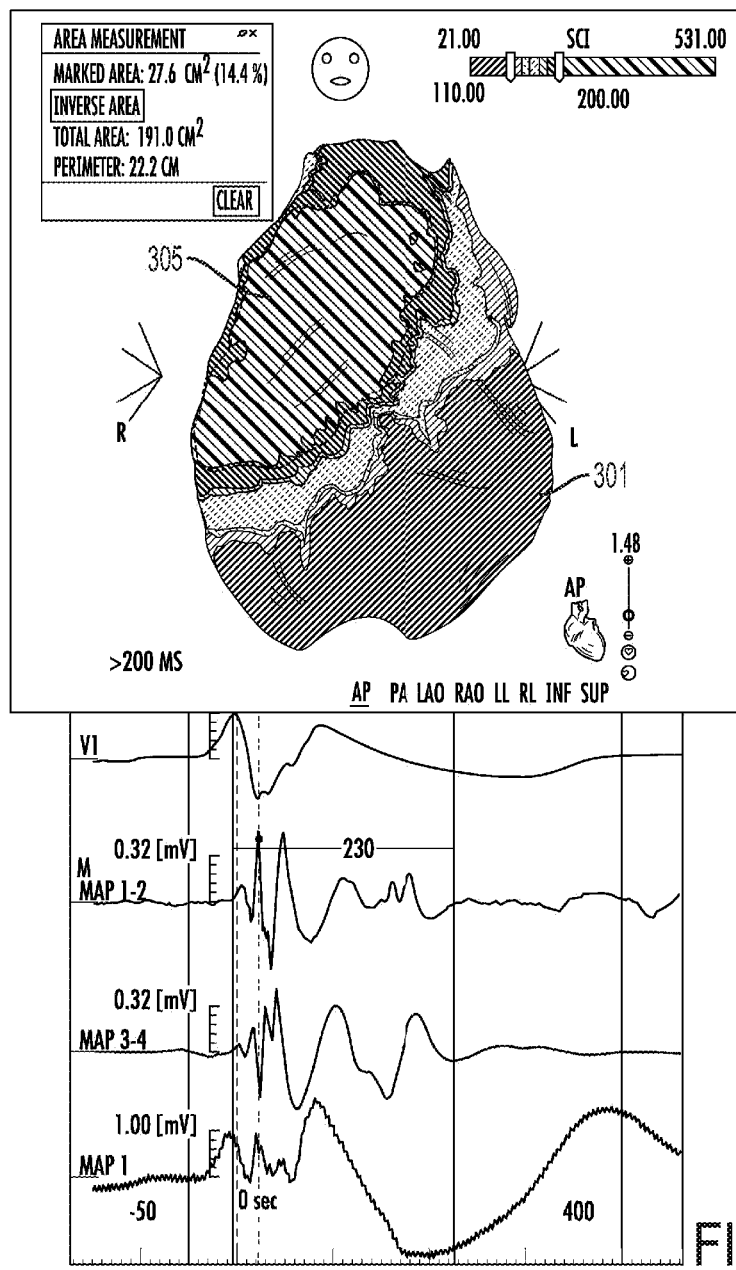

FIGS. 3A, 3B and 3C show Brugada Syndrome concentric substrate distribution, that is, each of these figures show an epicardial PDM after Class IC drug-challenge. The maps are reconstructed by collecting the duration of each bipolar EGM. The color-code (shown as different hatching patterns) ranges from red 301 to purple 305, where red 301 is showing regions exhibiting less than 110 ms duration. Purple 305 is representing areas with longer EGM duration (≥300 ms in FIG. 3A, ≥250 ms in FIG. 3B and ≥200 ms in FIG. 3C). Additional colors (not shown) represent areas >110 ms to 300 ms. According to the different cut-off applied, a concentric distribution is shown, where the longest potentials (≥300 ms duration) are located in the inner circle (FIG. 3A), whilst the relatively shorter ones, but still ≥200 ms, are in the outer circle (FIG. 3C). The regions showing longer potential duration have different dimensions (≥300 area is 5.9 cm2, ≥250 area is 14.7 cm2 and ≥200 ms area is 27.6 cm2, respectively). Below each map in FIGS. 3A, 3B, 3C, an example of the EGM recorded in the purple 305 area when the coved-type pattern occurs after ajmaline test is shown (EGMs of 322 ms, 255 ms and 230 ms duration in each panel of FIG. 3A, 3B, 3C, respectively).

The QRS complex is a name for the combination of three of the graphical deflections seen on a typical electrocardiogram, e.g., EGM or ECG. QRS is usually the central and most visually obvious part of the tracing. It corresponds to the depolarization of the right and left ventricles of the human heart. In adults, deflections normally last 0.06-0.10 seconds; in children and during physical activity, it may be shorter. The Q, R, and S waves occur in rapid succession, do not all appear in all leads, and reflect a single event, and thus are usually considered together. A Q wave is any downward deflection after the P wave. An R wave follows as an upward deflection, and the S wave is any downward deflection after the R wave. The T wave follows the S wave, and in some cases an additional U wave follows the T wave. The late activity is extended after the QRS termination and it is characterized by a fragmented and discrete late component. QRS represents simultaneous activation of the right and left ventricle.

In each EGM panel shown in the lower portion of FIGS. 3A, 3B and 3C, V1 ECG lead, distal, proximal bipolar and unipolar signals are shown at 200 mm/sec speed, from top to bottom, respectively.

The technique described herein will improve the existing process of manual measurements for duration map construction. The physician will no longer need to manually move and measure the two duration calipers for each point taken during duration map reconstruction. By using the present method to calculate each acquired point potential duration, the system can automatically annotate the ventricular EGMs duration from the onset to its offset, and automatically measure signals duration to create the PDM for Brugada syndrome substrate characterization.

Moreover, the process of prolonged EGMs detection and their quantification in terms of potential duration is enhanced by the present technique. This approach creates PDM with objective annotation, correctly identifying the adequate ablation target areas. The system automatically acquires bipolar and potential duration information by an ablation and/or multielectrode mapping (MEM) catheter to speed up the procedure. The method can be performed on two heart beats on the 2.5 seconds of the mapping bipolar signal of the acquired point, and the potential duration on the heart beat with the best positions stability can be selected. This enables positions stability to be considered in calculating potential duration, which cannot be done manually.

Figure 4A:
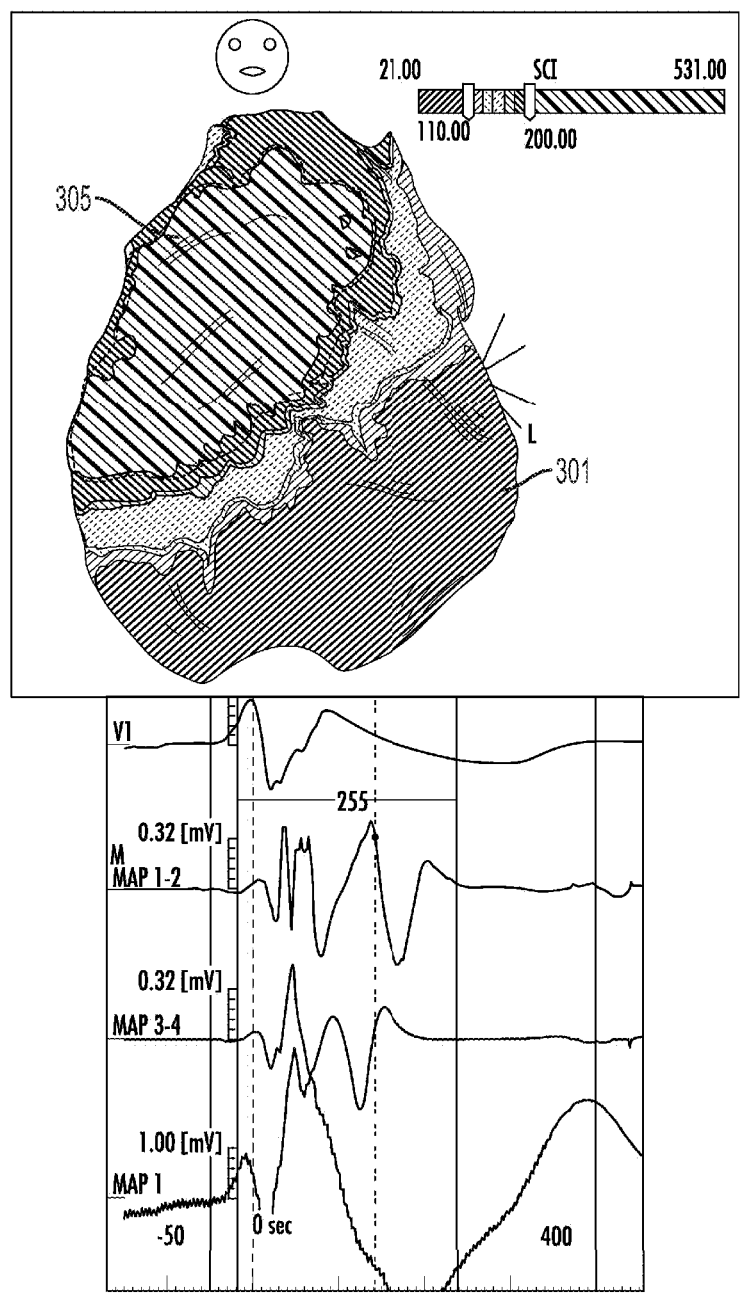
FIGS. 4A, 4B show a PDM before and after radiofrequency ablation.
Figure 4B:
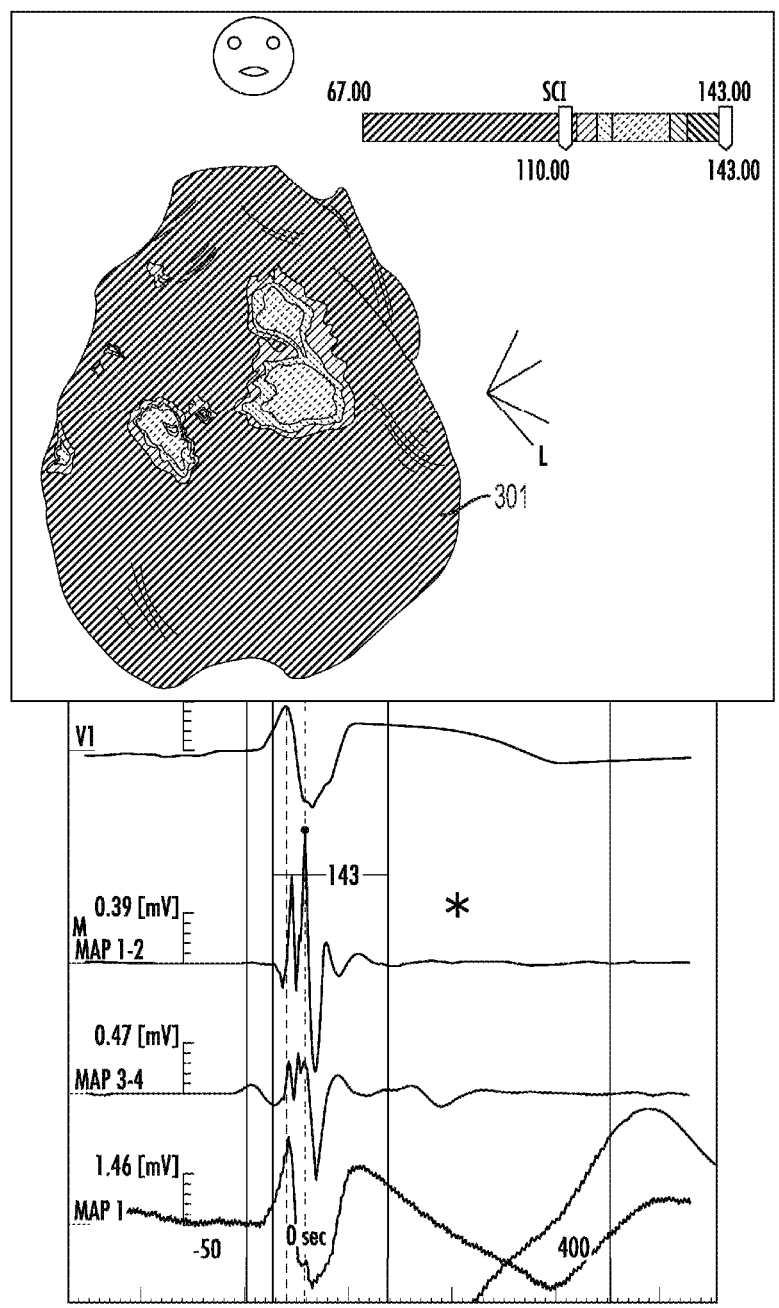

FIGS. 4A and 4B show a PDM before and after RF ablation. FIG. 4A top shows the PDM before ablation, while FIG. 4A bottom shows an example of prolonged and fragmented potential found in the purple area 305 (distal bipolar EGM 255 ms duration "DP-EMG"). After ablation, FIG. 4B top shows the PDM with the disappearance of abnormally prolonged EGMs, highlighting that the late component (activation after the QRS—peaks above 0.05 mV where Potential duration is bigger than 200 ms) has been abolished (EGMs duration of 143 ms; FIG. 4B bottom). The asterisk in FIG. 4B bottom indicates the disappearance of the late components that had been recorded prior to ablation. The EGM showed in FIG. 4B has been registered in the same region that was previously exhibiting the prolonged and fragmented potential, illustrated in FIG. 4A. In each EGM panel, V1 II ICS ECG lead, distal, proximal bipolar, and unipolar signals recorded are shown from top to bottom, respectively. Of note, in FIG. 4A bottom, the V1 lead is showing a typical coved-type pattern, whereas in FIG. 4B bottom, the same ECG lead is demonstrating that the BrS pattern has been modified, showing a horizontal and flat ST-segment elevation after ablation.

Figure 5:
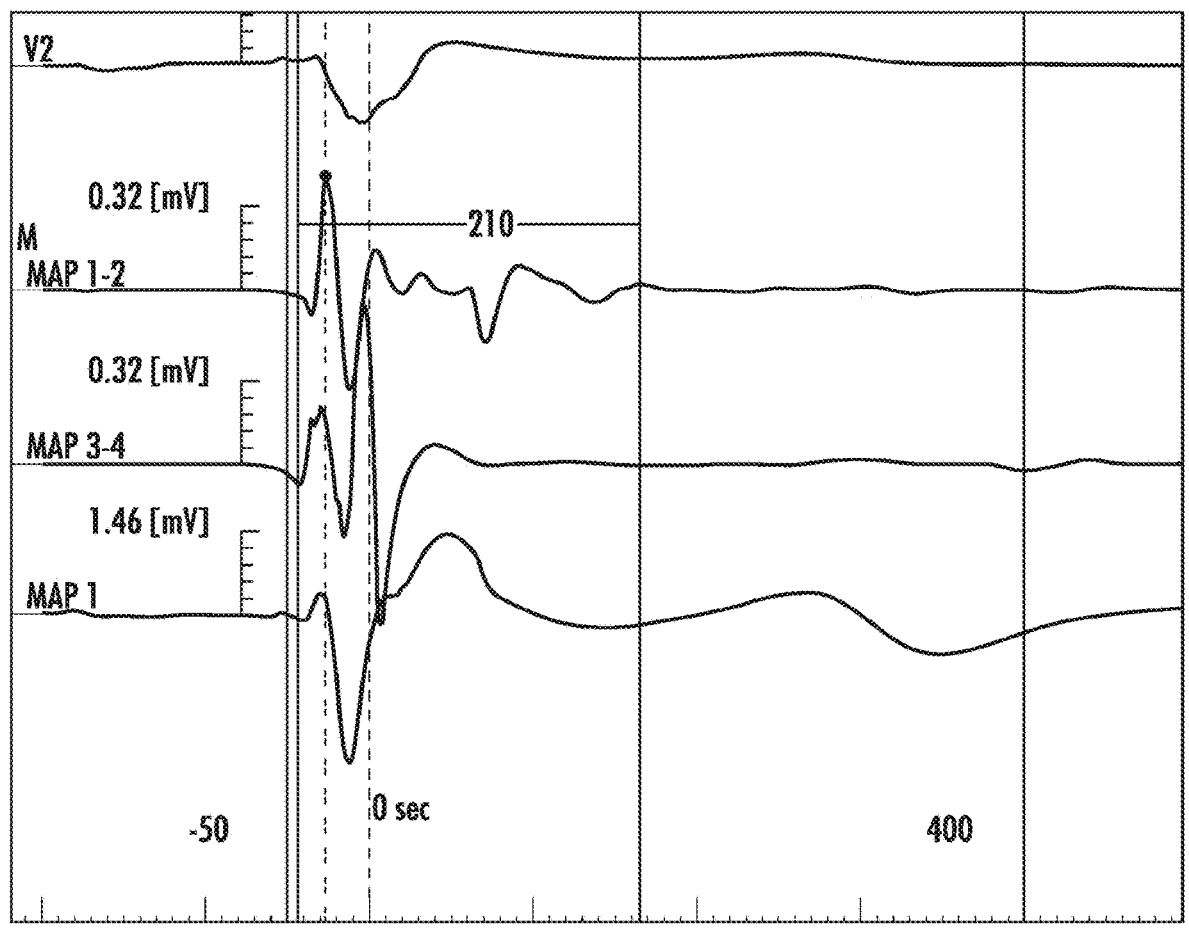
FIG. 5 shows a calculation of potential duration.

FIG. 5 shows a calculation of Potential Duration which is marked by the two vertical lines or borders, R1 and R2. These borders indicate WOI[−50,400] from 2000 ms−50 ms (1950 ms) to 2000 ms+400 ms (2400 ms). As shown, the Potential Duration is greater than 200 ms. Around the dotted vertical line is the QRS; the late component appears in the right part of the Potential Duration marked with the two borders R1 and R2.

Figure 6:
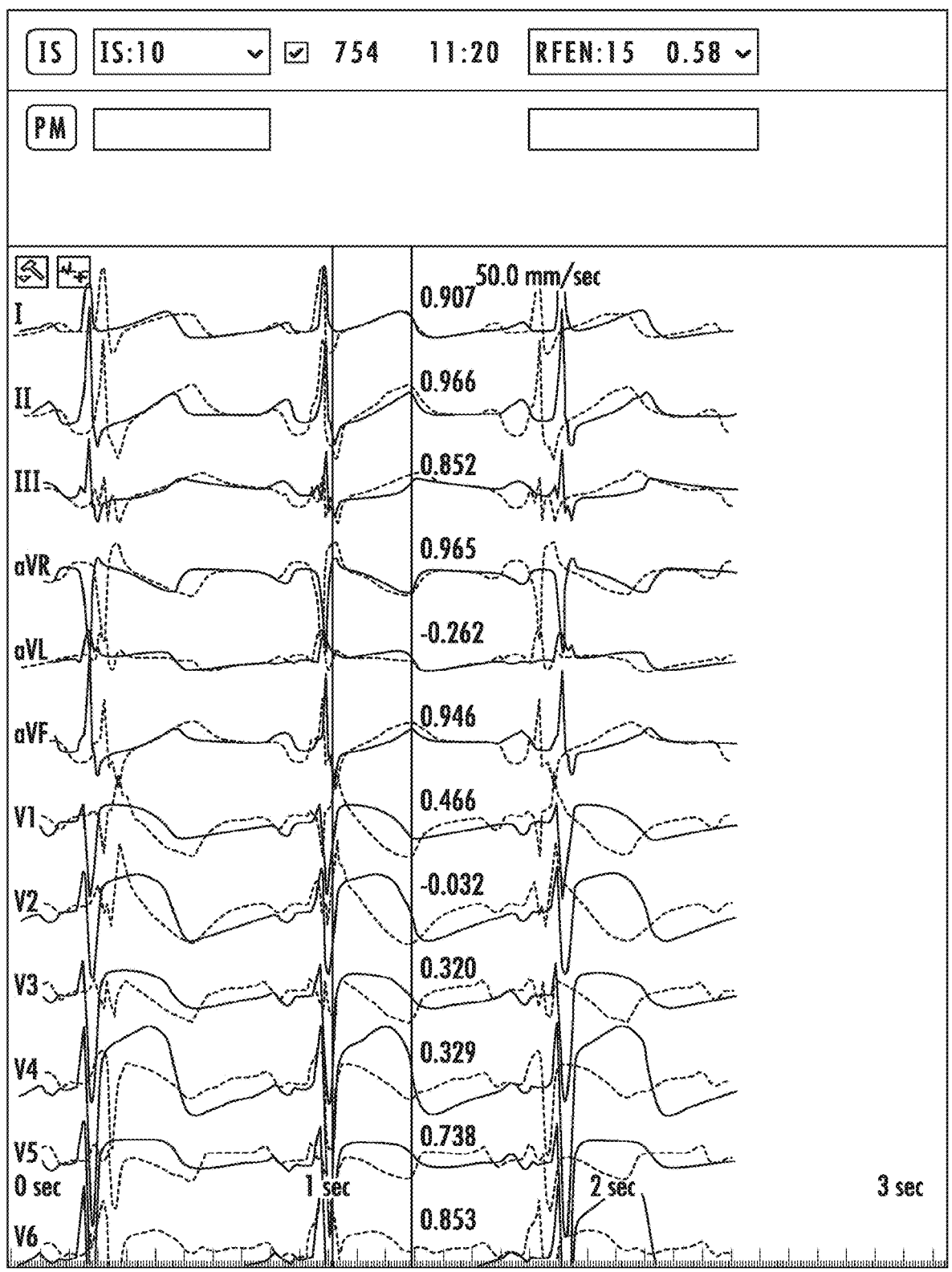
FIG. 6 shows changes in BS ECG signal.

FIG. 6 shows changes in BS ECG signal, that is, the changes of the BS ECG Signals 601 when the BrS is induced, and the BS ECG Signals 602 after treating the BrS with ablation. Accordingly, ECG 602 refers to end of class IC drug injection and ECG 601 refers to end of RF ablation.

Figure 7:
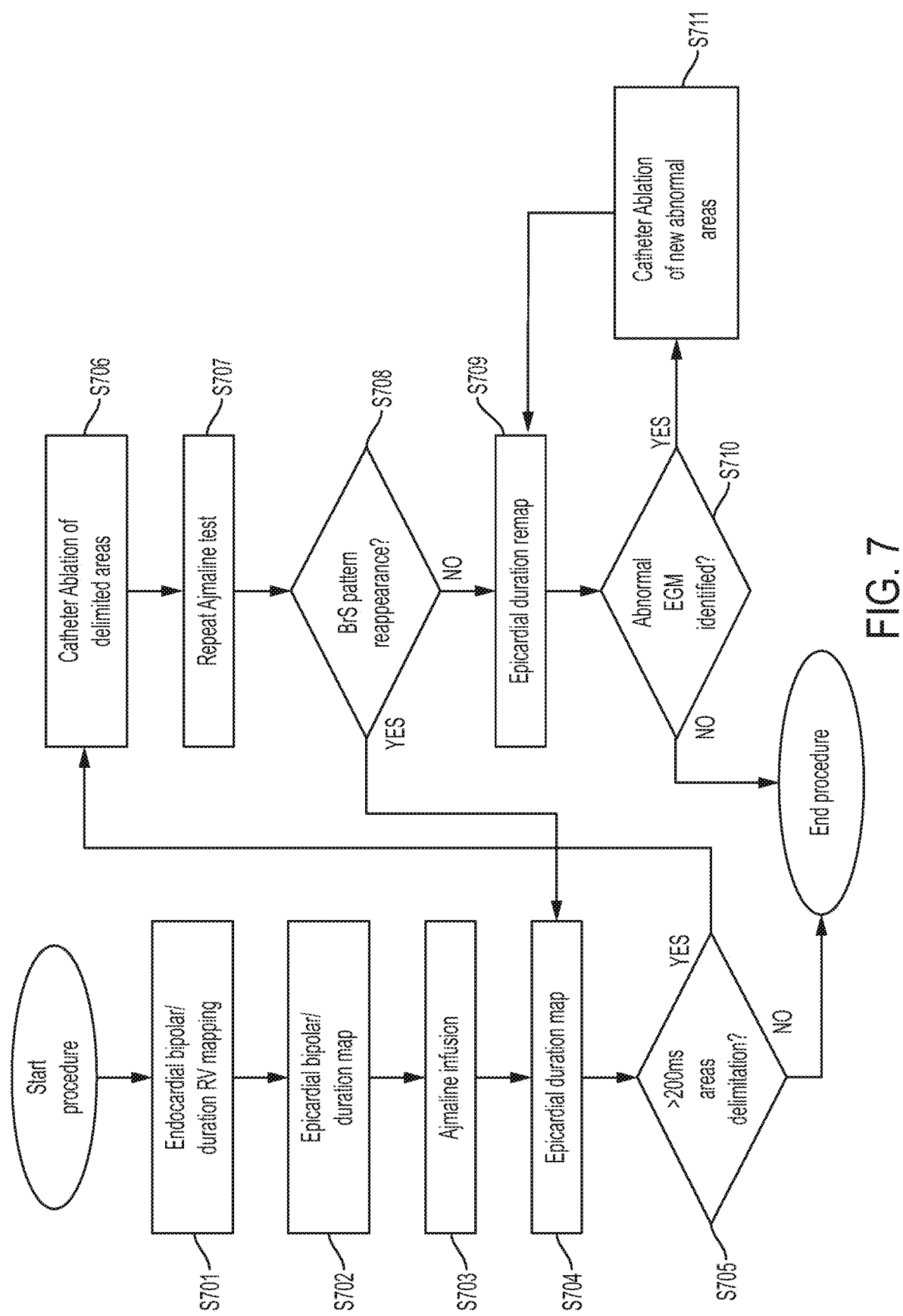
FIG. 7 is a work flow diagram of Brugada syndrome epicardial ablation in one embodiment.

FIG. 7 is a work flow diagram of Brugada syndrome epicardial ablation. In step S701, endocardial bipolar/duration RV mapping is performed. In step S702, epicardial bipolar/duration mapping is performed, creating a baseline PDM as shown, for example, in FIG. 1. In step S703, an ajmaline infusion is administered and an ajmaline test is performed. In step S704, an updated epicardial duration map, which maintains the fast anatomical mapping ("FAM") (anatomical volume) data and adds electro-anatomical data is produced. In step S705, it is determined whether or not there are areas of delimination, that is, areas in which the duration of potentials exceed a threshold amount, for example, a threshold greater than 200 ms. If so (S705=YES), in step S806 catheter ablation of the area(s) of delimination is performed. In step S707, the ajmaline test is repeated; this test had been initially performed in step S703.

In step S708, it is determined whether or not the BrS pattern reappears. If the BrS pattern does reappear (S708=YES), the procedure continues at step S704. If the BrS pattern does not reappear (S708=NO), at step S709, an updated epicardial duration re-map is created. In step S710, it is determined whether or not any abnormal EGMs are identified. If there are none (S710=NO), the procedure ends.

If one or more abnormal EGMs are identified (S710=YES), at step S711, catheter ablation of the new abnormal EGM areas is prepared and the process continues at step S709.

If the areas of delimination are less than or equal to 200 ms (S805=NO), then the procedure ends.

Figure 8:
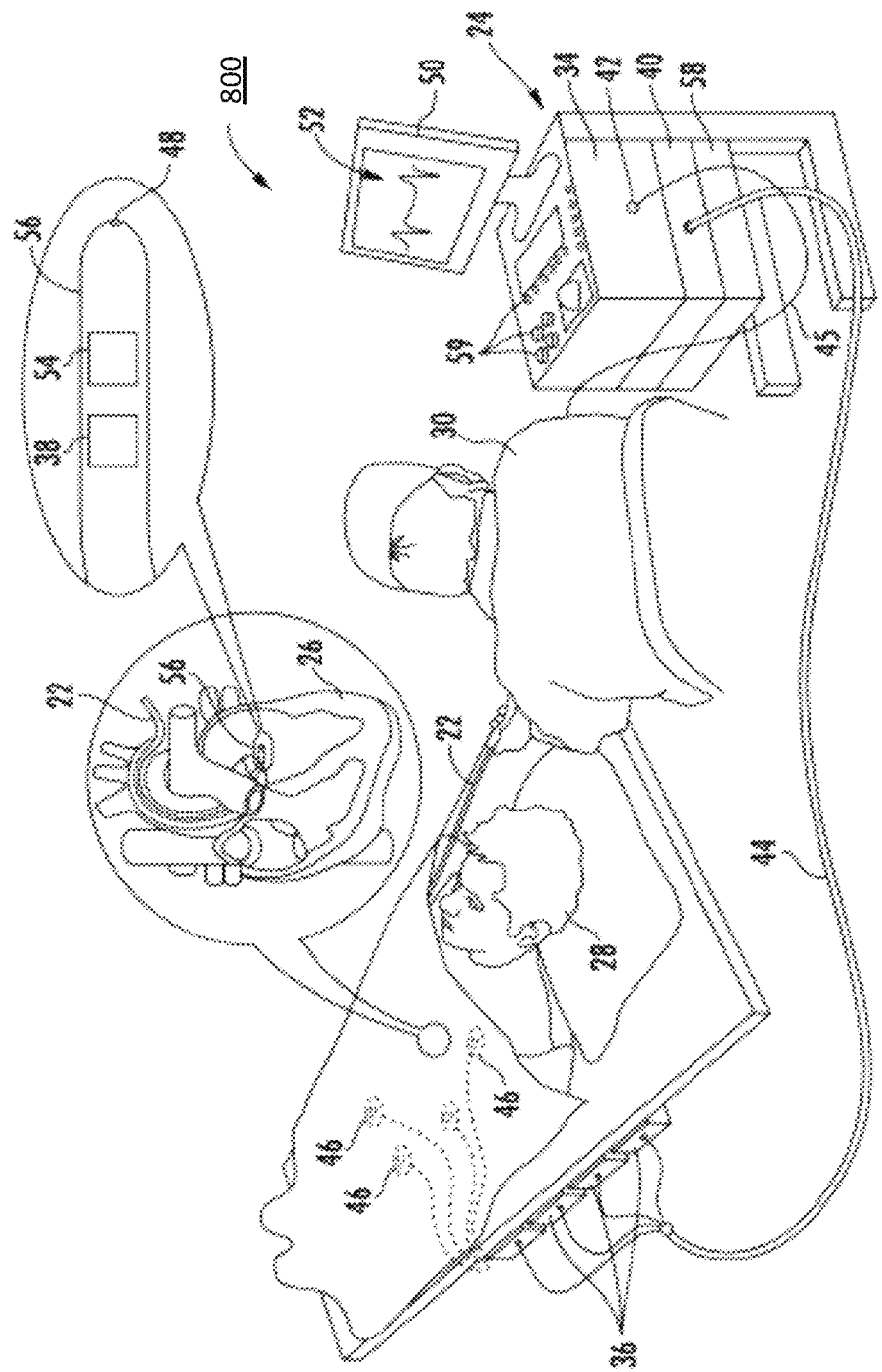
FIG. 8 shows an example mapping system for real-time mapping of cardiac ablation in accordance with an embodiment, in which the inventive technique is used.

FIG. 8 is an illustration of an example medical system 800 that may be used to generate and display information 52 (e.g., PDM and other maps and anatomical models of a portion of a patient and signal information). Tools, such as tool 22, can be any tool used for diagnostic or therapeutic treatment, such as for example, a catheter having a plurality of electrodes for mapping electrical potentials in a heart 26 of a patient 28. Alternatively, tools may be used, mutatis mutandis, for other therapeutic and/or diagnostic purposes of different portions of anatomy, such as in the heart, lungs or other body organs, such as the ear, nose, and throat (ENT). Tools may include, for example, probes, catheters, cutting tools and suction devices.

An operator 30 may insert the tool 22 into a portion of patient anatomy, such as the vascular system of the patient 28 so that a tip 56 of the tool 22 enters a chamber of the heart 26. The control console 24 may use magnetic position sensing to determine 3-D position coordinates of the tool (e.g., coordinates of the tip 56) inside the heart 26. To determine the position coordinates, a driver circuit 34 in the control console 24 may drive, via connector, 44, field generators 36 to generate magnetic fields within the anatomy of the patient 28.

The field generators 36 include one or more emitter coils (not shown in FIG. 8), placed at known positions external to the patient 28, which are configured to generate magnetic fields in a predefined working volume that contains a portion of interest of the patient anatomy. Each of the emitting coils may be driven by a different frequency to emit a constant magnetic field. For example, in the example medical system 800 shown in FIG. 8, one or more emitter coils can be placed below the torso of the patient 28 and each configured to generate magnetic fields in a predefined working volume that contains the heart 26 of the patient.

As shown in FIG. 8, a magnetic field location sensor 38 is disposed at the tip 56 of tool 22. The magnetic field location sensor 38 generates electrical signals, based on the amplitude and phase of the magnetic fields, indicating the 3-D position coordinates of the tool (e.g., position coordinates of the tip 56). The electrical signals may be communicated to the control console 24 to determine the position coordinates of the tool. The electrical signals may be communicated to the control console 24 via wire 45.

Alternatively, or in addition to wired communication, the electrical signals may be wirelessly communicated to the control console 24, for example, via a wireless communication interface (not shown) at the tool 22 that may communicate with input/output (I/O) interface 42 in the control console 24. For example, U.S. Pat. No. 6,266,551, whose disclosure is incorporated herein by reference, describes, inter alia, a wireless catheter, which is not physically connected to signal processing and/or computing apparatus and is incorporated herein by reference. Rather, a transmitter/receiver is attached to the proximal end of the catheter. The transmitter/receiver communicates with a signal processing and/or computer apparatus using wireless communication methods, such as IR, RF, Bluetooth, or acoustic transmissions. The wireless digital interface and the I/O interface 42 may operate in accordance with any suitable wireless communication standard that is known in the art, such as for example, IR, RF, Bluetooth, one of the IEEE 802.11 family of standards (e.g., Wi-Fi), or the HiperLAN standard.

Although FIG. 8 shows a single magnetic field location sensor 38 disposed at the tip 56 of tool 22, tools may include one or more magnetic field location sensors each disposed at any tool portion. The magnetic field location sensor 38 may include one or more miniature coils (not shown). For example, a magnetic field location sensor may include multiple miniature coils oriented along different axes. Alternatively, the magnetic field location sensor may comprise either another type of magnetic sensor or position transducers of other types, such as impedance-based or ultrasonic location sensors.

The signal processor 40 is configured to process the signals to determine the position coordinates of the tool 22, including both location and orientation coordinates. The method of position sensing described hereinabove is implemented in the CARTO™ mapping system produced by Biosense Webster Inc., of Diamond Bar, Calif., and is described in detail in the patents and the patent applications cited herein.

The tool 22 may also include a force sensor 54 contained within the tip 56. The force sensor 54 may measure a force applied by the tool 22 (e.g., the tip 56 of the tool) to the endocardial tissue of the heart 26 and generate a signal that is sent to the control console 24. The force sensor 54 may include a magnetic field transmitter and a receiver connected by a spring in the tip 56, and may generate an indication of the force based on measuring a deflection of the spring. Further details of this sort of probe and force sensor are described in U.S. Patent Application Publications 2009/0093806 and 2009/0138007, whose disclosures are incorporated herein by reference. Alternatively, the tip 56 may include another type of force sensor that may use, for example, fiber optics or impedance measurements.

The tool 22 may also include an electrode 48 coupled to the tip 56 and configured to function as an impedance-based position transducer. Additionally or alternatively, the electrode 48 may be configured to measure a certain physiological property, for example the local surface electrical potential (e.g., of cardiac tissue) at one or more locations. The electrode 48 may be configured to apply RF energy to ablate endocardial tissue in the heart 26.

Although the example medical system 800 may be configured to measure the position of the tool 22 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499 6,177,792, the disclosures of which are incorporated herein by reference. Impedance-based position tracking techniques are described, for example, in U.S. Pat. Nos. 5,983,126, 6,456,828 and 5,944,022, the disclosures of which are incorporated herein by reference.

The I/O interface 42 may enable the control console 24 to interact with the tool 22, the body surface electrodes 46 and any other sensors (not shown). Based on the electrical impulses received from the body surface electrodes 46 and the electrical signals received from the tool 22 via the I/O interface 42 and other components of medical system 900, the signal processor 40 may determine the location of the tool in a 3-D space and generate the display information 52, which may be shown on a display 50.

The signal processor 40 may be included in a general-purpose computer, with a suitable front end and interface circuits for receiving signals from the tool 22 and controlling the other components of the control console 24. The signal processor 40 may be programmed, using software, to perform the functions that are described herein. The software may be downloaded to the control console 24 in electronic form, over a network, for example, or it may be provided on non-transitory tangible media, such as optical, magnetic or electronic memory media. Alternatively, some or all of the functions of the signal processor 40 may be performed by dedicated or programmable digital hardware components.

In the example shown at FIG. 8, the control console 24 is connected, via cable 44, to body surface electrodes 46, each of which are attached to patient 28 using patches (e.g., indicated in FIG. 8 as circles around the electrodes 46) that adhere to the skin of the patient. Body surface electrodes 46 may include one or more wireless sensor nodes integrated on a flexible substrate. The one or more wireless sensor nodes may include a wireless transmit/receive unit (WTRU) enabling local digital signal processing, a radio link, and a miniaturized rechargeable battery. In addition or alternative to the patches, body surface electrodes 46 may also be positioned on the patient using articles worn by patient 28 which include the body surface electrodes 46 and may also include one or more position sensors (not shown) indicating the location of the worn article. For example, body surface electrodes 46 can be embedded in a vest that is configured to be worn by the patient 28. During operation, the body surface electrodes 46 assist in providing a location of the tool (e.g., catheter) in 3-D space by detecting electrical impulses generated by the polarization and depolarization of cardiac tissue and transmitting information to the control console 24, via the cable 44. The body surface electrodes 46 can be equipped with magnetic location tracking and can help identify and track the respiration cycle of the patient 28. In addition to or alternative to wired communication, the body surface electrodes 46 may communicate with the control console 24 and one another via a wireless interface (not shown).

During the diagnostic treatment, the signal processor 40 may present the display information 52 and may store data representing the information 52 in a memory 58. The memory 58 may include any suitable volatile and/or non-volatile memory, such as random access memory or a hard disk drive. The operator 30 may be able to manipulate the display information 52 using one or more input devices 59. Alternatively, the medical system 800 may include a second operator that manipulates the control console 24 while the operator 30 manipulates the tool 22. It should be noted that the configuration shown in FIG. 8 is exemplary. Any suitable configuration of the medical system 800 may be used and implemented.

Figure 9:
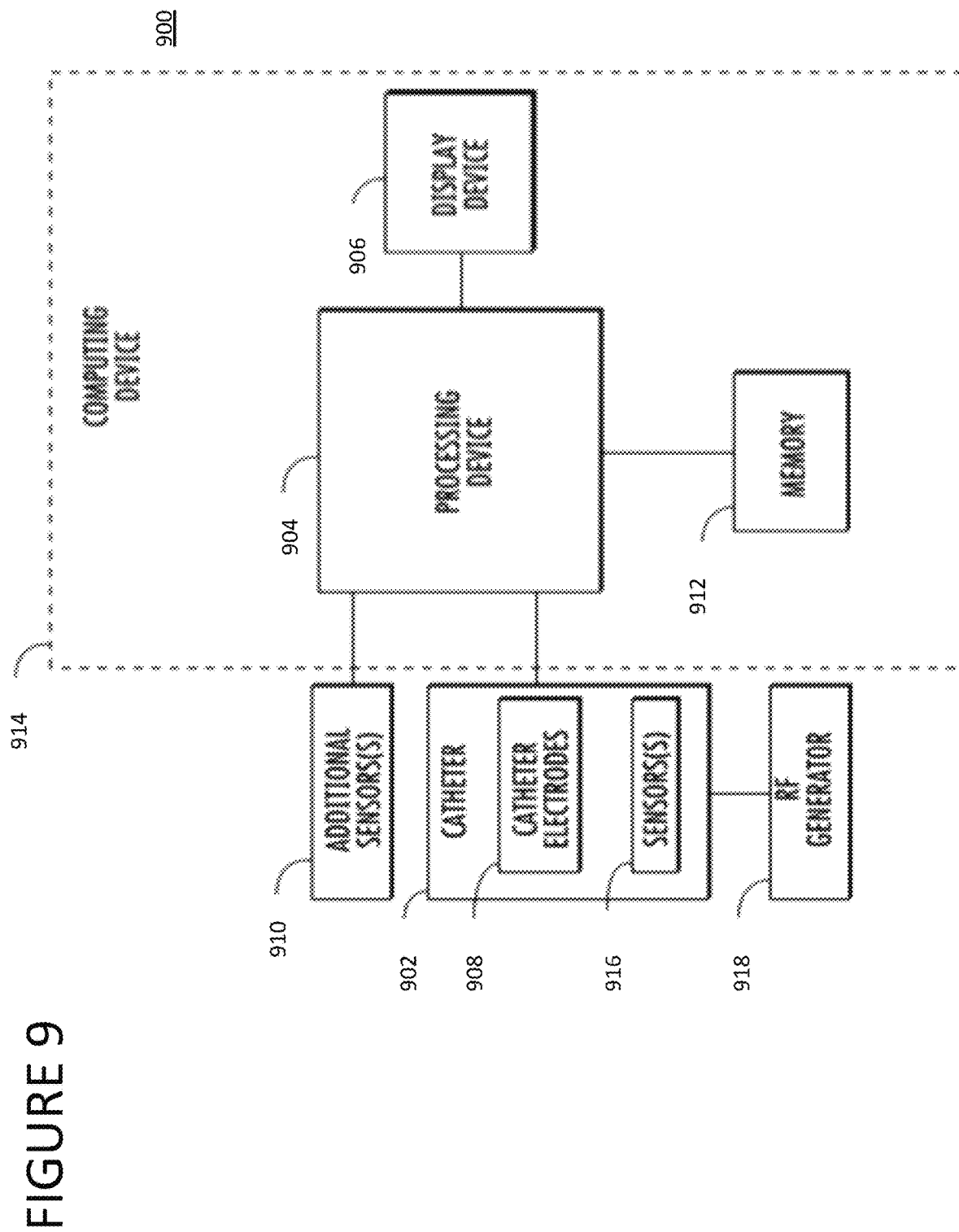
FIG. 9 is a block diagram illustrating example components of a medical system in one embodiment.

FIG. 9 is a block diagram illustrating example components of a medical system 900 in which features described herein can be implemented. As shown in FIG. 9, the system 900 includes catheter 902, processing device 904, display device 906 and memory 912. As shown in FIG. 9, the processing device 904, display device 906 and memory 912 are a part of computing device 914. In some embodiments, the display device 906 may be separate from computing device 914. Computing device 914 may also include an I/O interface, such as I/O interface 42 shown in FIG. 9.

Catheter 902 includes a plurality of catheter electrodes 908 for detecting the electrical activity of the heart over time. Catheter 902 also includes sensor(s) 916, which include, for example, sensors (e.g., a magnetic field location sensor) for providing location signals to indicate the location of the catheter 902 in a 3-D space as well as sensors (e.g., position sensors, pressure or force sensors, temperature sensors, impedance sensors) for providing ablation parameter signals during the ablation of the heart tissue. The example system 900 also includes one or more additional sensors 910, separate from the catheter 902, used to provide location signals indicating the location of the catheter 902 in a 3D space.

The system 902 shown in example system 900 also includes an RF generator 918, which supplies high-frequency electrical energy, via catheter 902, for ablating tissue at locations engaged by the catheter 902. Accordingly, catheter 902 may be used to acquire electrical activity for generating mapping of the heart as well ablating cardiac tissue. As described above, however, embodiments may include catheters used to acquire the electrical activity for generating mapping of the heart while not used to ablate cardiac tissue.

Processing device 904 may include one or more processors each configured to process the ECG signals, record ECG signals over time, filter ECG signals, fractionate ECG signals into signal components (e.g., slopes, waves, complexes) and generate and combine ECG signal information for displaying the plurality of electrical signals on display device 906. Processing device 904 may also generate and interpolate mapping information for displaying maps of the heart on display device 906. Processing device 904 may include one or more processors (e.g., signal processor 40) configured to process the location information acquired from sensors (e.g., additional sensor(s) 910 and catheter sensor(s) 916) to determine location and orientation coordinates.

Processing device 904 is also configured to drive display device 906 to display dynamic maps (i.e., spatio-temporal maps) of the heart and the electrical activity of the heart using the mapping information and the ECG data. Display device 906 may include one or more displays each configured to display maps of the heart representing spatio-temporal manifestations of the electrical activity of the heart over time and display the ECG signals acquired from the heart over time.

The catheter electrodes 908, catheter sensor(s) 916 and additional sensor(s) 910 may be in wired or wireless communication with processing device 904. Display device 906 may also be in wired or wireless communication with processing device 904.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

An example study employing the present method is presented. In this example study, a patient population is obtained comprising consecutive selected symptomatic patients diagnosed with type 1 BrS-ECG pattern either spontaneously or after ajmaline administration; each patient also had an ICD implanted. Ajmaline administration (1 mg/Kg in 5 minutes) was considered positive if the typical coved-type ECG pattern appeared in more than one right precordial lead (V1-V3).

Figure 11:
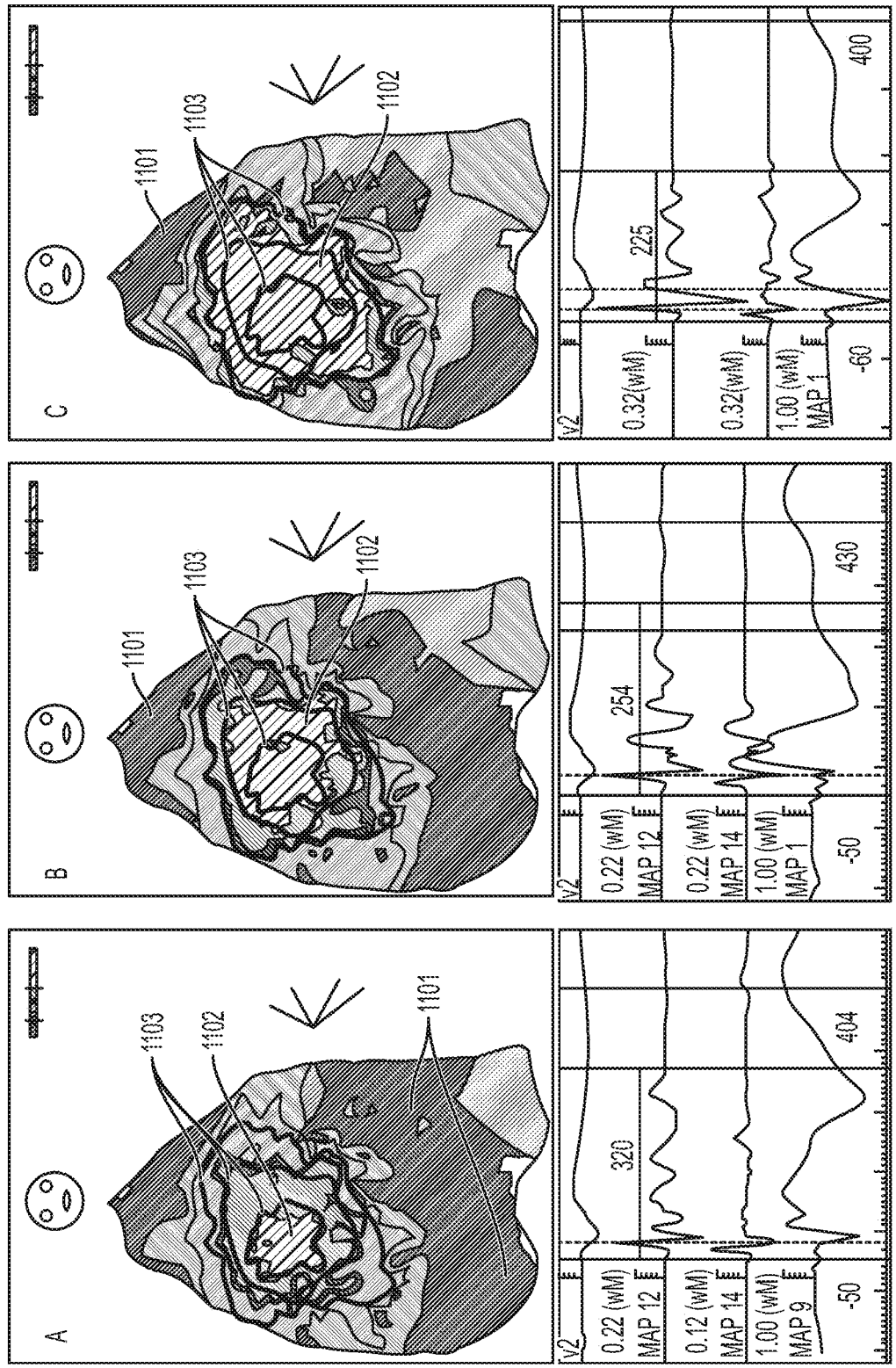
FIG. 11 illustrates additional test results for one patient.
Figure 12:
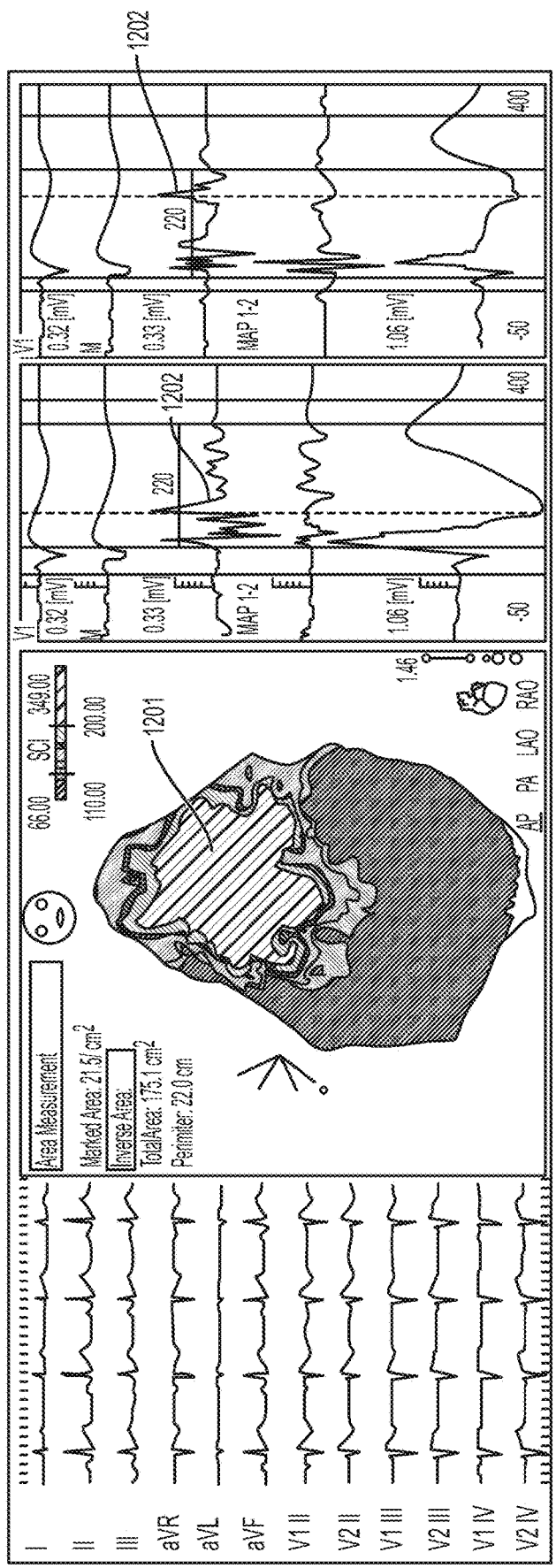
FIG. 12 shows a spontaneous type 1 Brugada pattern for one patient.

Patients underwent a combined epi-endocardial mapping procedure (examples of mapping shown in FIGS. 10-15, described below). Under general anesthesia, an invasive arterial pressure line was obtained through radial artery access. The ECG was continuously recorded during the procedure. After femoral venous access, a multipolar diagnostic catheter was positioned at the RV apex. The epicardial access was gained by a percutaneous subxyphoid access to the pericardial space, as is known in the art. Three dimensional RV endocardial and epicardial mapping, using CARTO® 3, was performed in all patients during stable sinus rhythm and presence of type 1 BrS-ECG pattern. Epicardial mapping was systematically performed after endocardial mapping, in order to have adequate delimination of the RV boundaries when mapping the epicardium. Epicardial RV mapping and ablation catheter manipulation were assisted by a steerable sheath, such as Agilis EPI, St. Jude Medical, St. Paul, Minn. BrS epicardial substrate identification consisted in mapping the entire RV epicardial surface under baseline conditions and after ajmaline infusion (imp/Kg in 5 minutes). Three groups of RV epicardial electrograms properties are obtained using a CARTO® 3 mapping system: 1) bipolar/unipolar voltage map, 2) local activation time map (LAT), and 3) potential duration map (PDM) in which abnormal long-duration bipolar electrograms were defined as low-frequency (up to 100 Hz) prolonged duration (>200 ms) bipolar signals with delayed activity extending beyond the end of the QRS complex. FIGS. 10-12, which are described below, illustrate this. The bipolar electrograms were filtered from 16 Hz to 500 Hz, displayed at a speed of 200 ms and were recorded between the distal electrode pair. Electrograms were excluded if their technical quality was insufficient or if catheter-induced extrasystoles occurred.

Voltage mapping, in this example study is described as follows. Color-coded electroanatomical voltage (not shown), activation (not shown) and duration maps (shown in FIG. 10A, 10B, 10C using various hash patterns to indicate various colors) were performed and superimposed to cardiac anatomy. Red color 1003 indicates low-voltage dense scar that arbitrarily was defined as bipolar signal amplitude <0.5 mV, while purple color 1001 indicates voltage areas >1.5 mV. Areas of low voltage were identified using standard voltage cut-off values for dense scar (<0.5 mV) and border zone (BZ) (<1.5 mV). Electrograms below the 0.05 mV threshold were not considered.

LAT mapping in this example study is described as follows. To study activation, the local activation time was assessed, defined as the interval (in milliseconds) from a peak of QRS in lead II to the steepest negative change in voltage over time (dV/dt) of the intrinsic deflection in the bipolar electrogram. Activation-duration was defined as the interval (in milliseconds) between the earliest activation time of any electrogram (activation-start) and the latest activation time of any electrogram (activation-end).

Potential Duration Mapping (PDM) in this example study is described as follows. The maximum electrogram duration was the longest electrogram with continuous deflections without an intervening isoelectric line as recorded with a 0.45 sec window of interest (WOI). Fractionation of electrograms was defined as the presence of more than two intrinsic deflections and expressed as number of intrinsic deflections per electrogram. Electrogram duration was measured before and after ajmaline in the bipolar signal as the interval between the onset of the first and the offset of the last component of the electrogram, measured at the time scale of 200 mm/sec, and expressed as mean bipolar electrogram duration (in milliseconds). A cut-off range from 100 ms to 200 ms, 250 ms and 280 ms was used for defining color-coded duration maps. As a result, a color-code map was obtained showing the regions displaying the shortest (<110 ms cut-off, red 1003) and the longest duration (>200 ms cut-off, purple 1001), respectively. The degree of duration of the potentials was displayed from the longest (purple 1001) to the shortest potential (red 1003) using different duration cut-off values (illustrated in FIGS. 10-14). According to the selected cut-offs, three different concentric circles were drawn around purple areas as shown in FIG. 11. The PDM was performed by collecting the duration of each bipolar electrogram using the CARTO® 3 system.

Substrate-based ablation in this example study is described as follows. Epicardial ablation was performed during sinus rhythm using a stepwise strategy in a descending order of abnormal potential duration as displayed on the map and beginning from the longest potentials. The longest-duration potential area was displayed in purple by setting the color-bar upper limit (300 ms) in the three-dimensional duration map, as created simultaneously during voltage and LAT mapping. Afterwards, RF ablation was performed sequentially by gradually moving at substrate sites towards areas with less prolonged late (250 ms and 200 ms) potentials according to the stepwise strategy. RF was delivered with an externally irrigated 3.5 mm tip ablation catheter. A power control mode having from 35 W up to 45 W was used. The irrigation rate was 17 mL/min for RF ablation, which was delivered by a dragging strategy, up to complete elimination of all long-duration, delayed activity.

Figure 15:
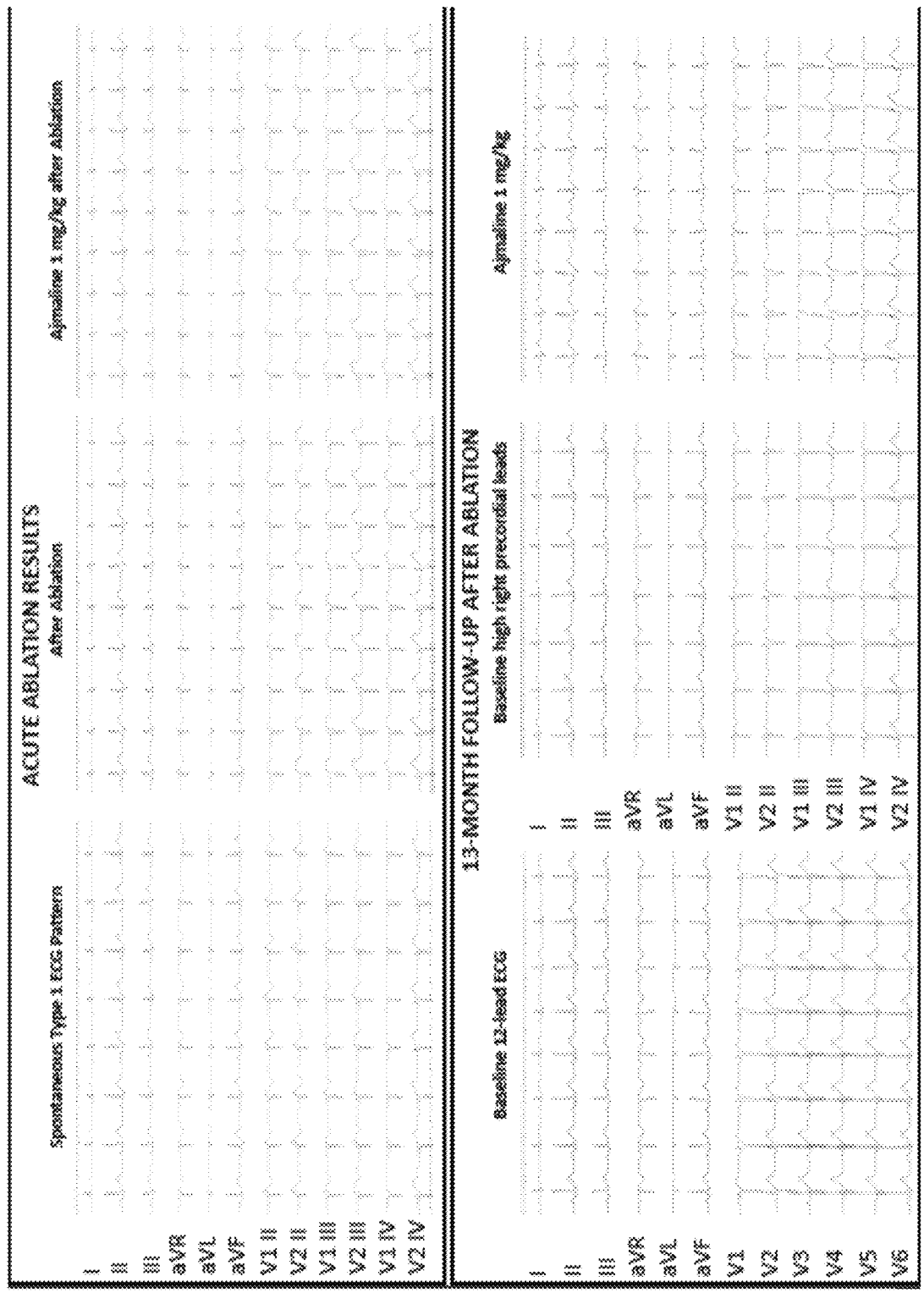
FIG. 15 shows ECG changes for the example patient.

FIG. 15 shows BrS-ECG pattern changes during epicardial RF ablation that were analyzed by continuous ECG monitoring. The ST-segment modifications were evaluated using a correlation software, such as PASO in CARTO® 3. Immediate ablation endpoint was the elimination of all abnormally prolonged late activity with normalization of BrS-ECG pattern, as shown in FIG. 15.

Ajmaline was systematically re-infused after RF ablation to ensure abolition of all abnormal ventricular potentials while confirming the BrS-ECG pattern elimination. In patients in whom the BrS-ECG pattern reappeared during infusion, epicardial duration maps were repeated to identify any residual or additional abnormal signals for further RF applications in order to definitively normalize the ECG pattern. Once a stable BrS-ECG pattern elimination was obtained, VT/VF inducibility was assessed. Intrapericardial liquid was permanently withdrawn through the deflectable sheet during the procedure to avoid serum accumulation.

The end-point of the example study was elimination of all abnormal electrical ventricular potentials before and after ajmaline, leading to ECG normalization and non-inducibility of ventricular tachycardia (VT) with respect to ventricular fibrillation (VF), e.g., VT/VF.

BrS was diagnosed in the presence of a coved-type ST elevation of >2 mm as documented in more than one lead from V1 to V3 positioned in the second, third, or fourth intercostal space. Because of the variable nature of the BrS-ECG pattern, BrS patients were classified according to their ECG at the time of the presentation and defined as spontaneous ECG pattern. Three BrS patient groups (BrS-1 to BrS-3) were defined as coved-type (BrS-1), saddleback ST configuration (BrS-2), and either type 1 or type 2 but with <2 mm of ST segment elevation (BrS-3). BrS patients with typical BrS-related symptoms included those with documented VF or polymorphic VT at the time of symptoms. BrS patients without typical BrS-related symptoms were considered as patients with different symptoms (from dizziness to palpitations) without ECG documentation at the time of events but all with inducible VT/VF. Patients with the worst clinical presentation were defined as those who experienced cardiac arrest or syncope due to documented ventricular fibrillation. A proband was defined as the first patient diagnosed with Brugada syndrome in a family on the basis of a type 1 Brugada ECG pattern. Major complications were defined as those that required prolonged hospitalization.

Procedural data in the example study include the following. The median procedure, fluoroscopy and RF application times were 169 minutes (Inter-quartil (IQR) 160-214, min-max 105-266), 8 minutes (IQR 7-9, min-max 6-14) and 18 minutes (IQR 17-21, min-max 12-31), respectively. During the procedure, the activation, voltage and duration maps were successfully acquired during sinus rhythm and after ajmaline-induced type 1 BrS-ECG pattern in all patients. At baseline, epicardial activation started in the lower septum/apex and subsequently diverged toward the tricuspid annulus and RVOT. As shown in FIGS. 10-14, for example, the red areas indicate short activation times while blue areas indicate longer activation times. No apparent conduction block was observed in any patient. After ajmaline infusion, the epicardial activation time was slightly longer without change in the sequence activation pattern, but this difference was not statistically significant, as shown in the table in FIG. 16. Overall, electro-anatomical voltage maps showed very small low-voltage areas in RVOT, which were larger in Group 1, particularly in patients with the worst clinical presentation than in Group 2 (P<0.001 as shown in FIG. 16). Before and after ajmaline, 3D epicardial duration maps displayed large areas of variable size with abnormally prolonged potentials in the RVOT, which contrasted with normal signals in the surrounding areas.

Electrophysiciological substrate characteristics according to spontaneous ECG pattern in the example study are as follows. Baseline clinical and ECG characteristics did not differ between the two groups including patients with the worst clinical presentation; spontaneous type 1 BrS-ECG pattern was less frequently found regardless of clinical presentation, as shown in the table in FIG. 17. CARTO® 3 maps identified epicardial areas of abnormal prolonged electrical signals over the RVOT (>75%) extending after ajmaline to RV free wall (see FIGS. 10-14). The area of electrical substrate significantly increased in size after ajmaline in both groups as shown in the table in FIG. 16. Before and after ajmaline, Group 1 showed wider area and more prolonged and abnormal potentials than Group 2, although the increase in Group 2 was three times higher as compared with baseline values shown in the table in FIG. 16. Of note, regardless of clinical presentation, before and after ajmaline the epicardial electrical substrate was larger in men than women. Areas with the longest abnormal potentials (>280 ms) in different RV regions appeared on color-coded maps to be smaller, displaying a characteristic onion-like substrate of concentric circles showing in the center of the area with the widest electrograms (see FIG. 11).

Electrophysiological substrate characteristics according to spontaneous ECG pattern in the example study are described as follows. There was no difference in clinical characteristics between patients with and without spontaneous type 1 ECG pattern including age, sex, or family history of sudden death of those less than 45 years old. Large abnormal areas and wider abnormal electrograms were found in patients with type 1 ECG pattern than in patients without. The localization of abnormal areas did not differ between patients with and without type 1 ECG pattern. Baseline ST segment elevation did not differ between Group 1 and Group 2, but after ajmaline the increase was significantly higher in Group 1. Overall, after ajmaline the degree of type 1 ST-segment elevation correlated with the magnitude of the wider area (r=0.682, p<0.001).

Substrate-based epicardial ablation in the example study can be described as follows. Once the areas targeted for ablation were established on the map of electrogram duration, RF started beginning on areas with the widest electrical potentials, which during ablation disappeared without significant change in voltage-amplitude after RF was turned off.

Elimination of abnormal signals was confirmed by remap and ajmaline reinfusion. Seventy-eight patients after ajmaline reinfusion showed reappearance of suspicious coved ECG pattern requiring further RF ablation to eliminate any residual abnormal potentials. Ablation at these sites eliminated the type 1 ECG pattern with successful suppression of VT/VF. Characteristically, during initial delivery of RF energy on the longest potential duration areas, the type 1 ECG pattern increased for some seconds, to progressively invert the ST segment slope from descending to ascending (see FIG. 12), and the increase was higher in Group 1. Immediately after, there was a typical flat ST-segment elevation progressively becoming ascendant in V1 and V2, which was not further modified by ajmaline and isoproterenol infusion.

FIGS. 10-17 illustrate the example study. Note that different hatching patterns are used to show different colors, e.g., color-coding, in FIGS. 10-15. FIGS. 10 and 11 illustrate a 39-year-old Brugada Syndrome (BrS) patient, presenting with a family history of BrS and syncope, who had an ICD implantation. The patient had positive ajmaline test and VT/VF inducibility during an electrophysiological study.

Figure 10A:
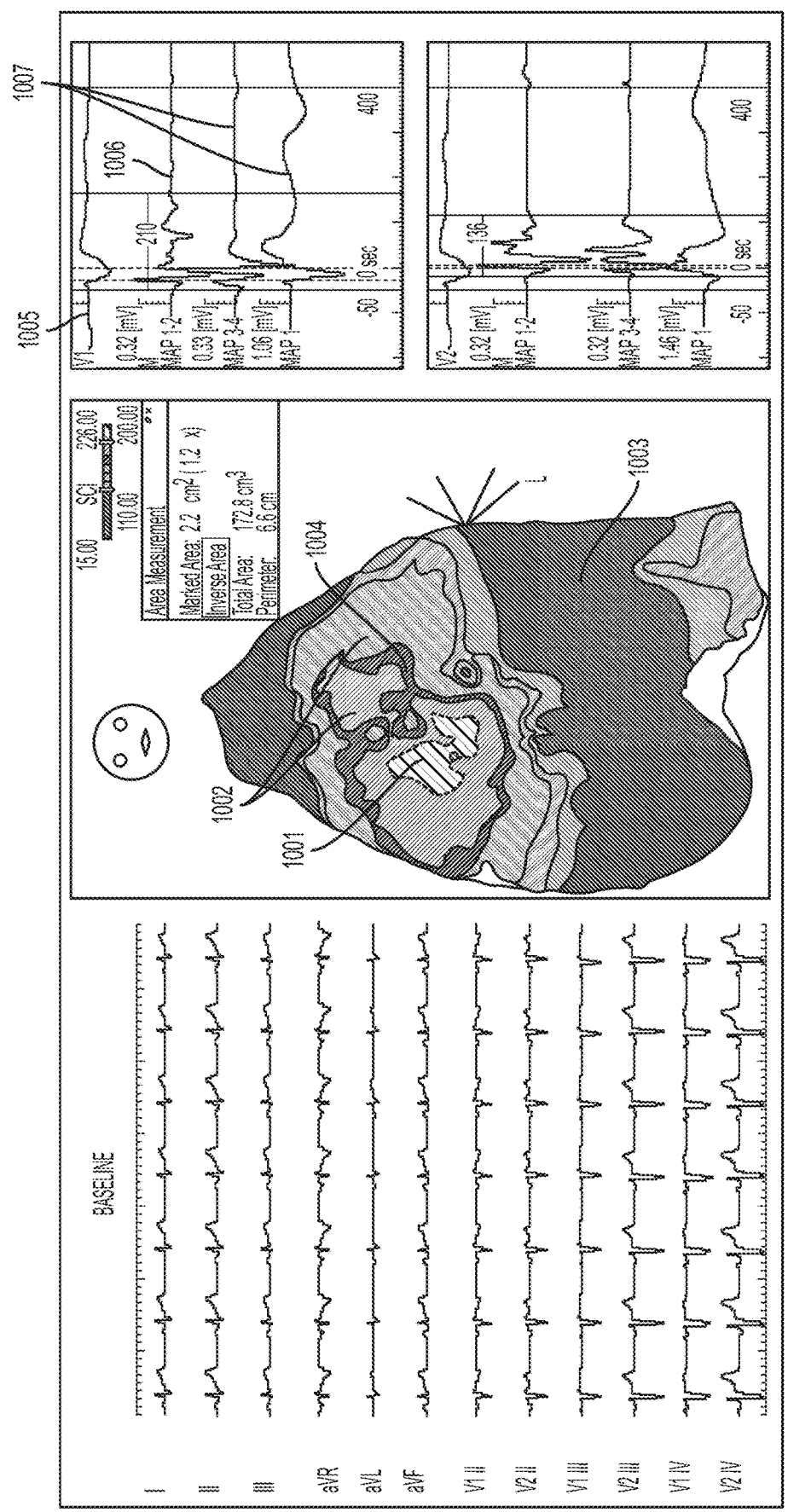
FIGS. 10A, 10B, 10C illustrate test results for one example patient.

FIG. 10A shows baseline BrS-ECG pattern and epicardial color-coded duration CARTO® maps. A saddle-back pattern is evident in V2 (II intercostal space) with a corresponding small (2.2 cm2) purple area 1001 of abnormally prolonged potentials (210 ms in the example). The border-zone area (green/blue area 1002 greater than 110 ms and less than 200 ms) shows potentials with relatively shorter duration (136 ms).

Figure 10B:
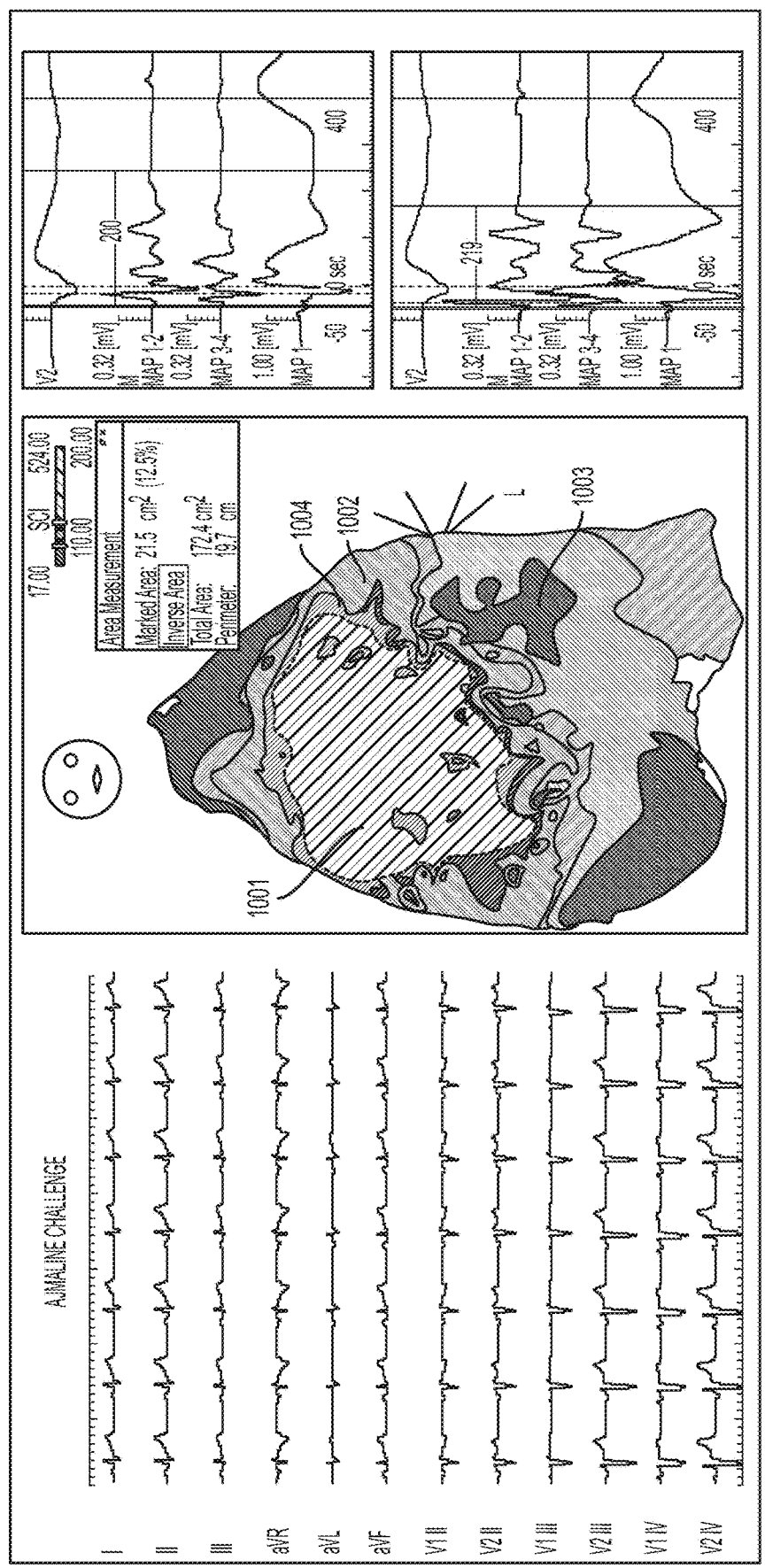

FIG. 10B shows BrS-ECG pattern and color-coded duration maps after ajmaline. After type 1 ajmaline-induced ECG pattern, the abnormal purple area 1001 significantly increased to 21.5 cm2. Examples of abnormal and prolonged electrograms (EGMs) found in the purple area 1001 after ajmaline test are shown beside the map (289 ms and 219 ms).

Figure 10C:
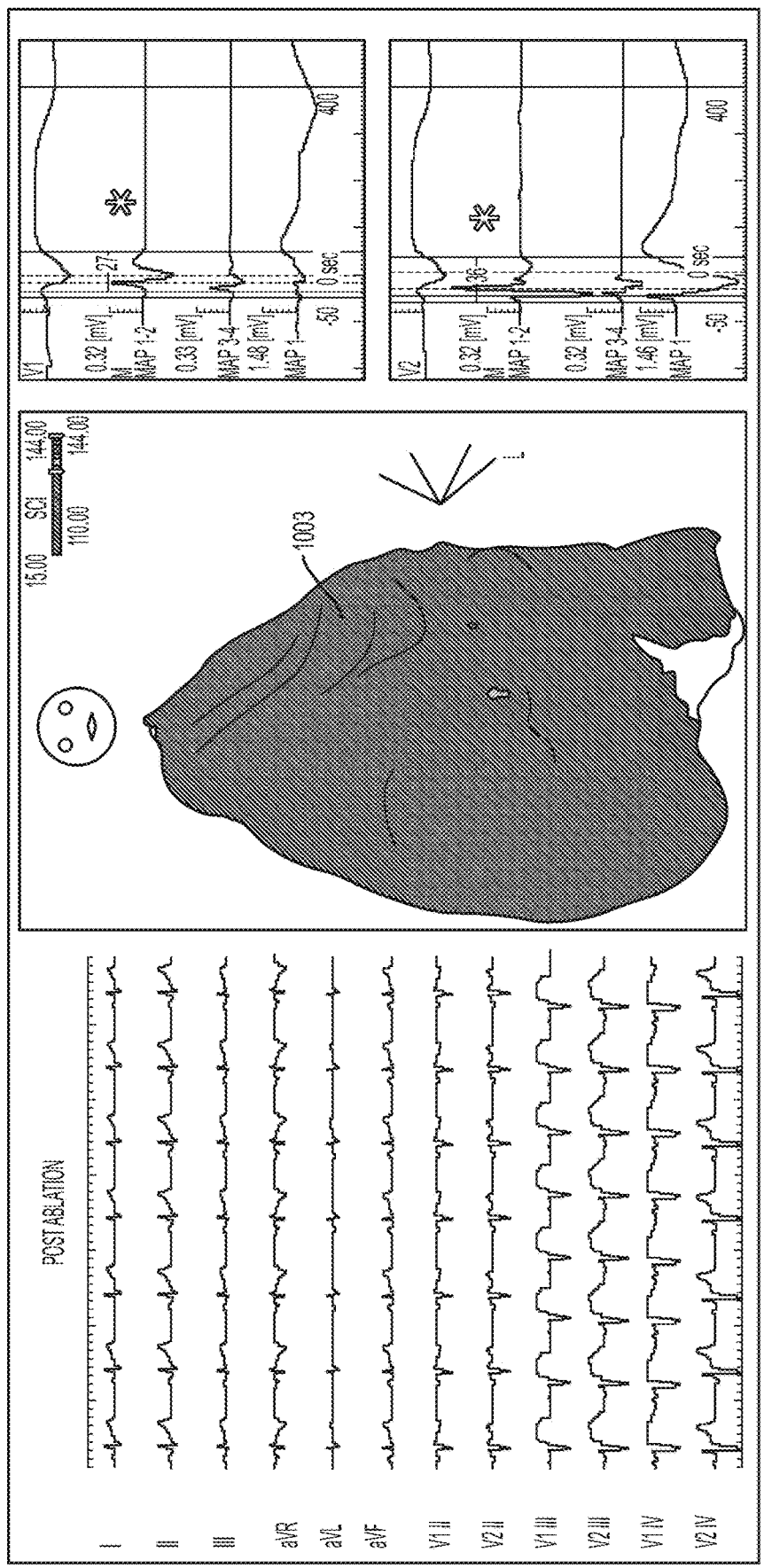

FIG. 10C shows BrS-ECG pattern and color-coded duration maps after RF ablation of epicardial substrate. After ajmaline re-challenge at the end of the procedure, the ECG showed a horizontal and ascendant ST-segment elevation, with minimal intraventricular conduction delay characterized by slight QRS broadening with a more pronounced S wave in leads I and II and qR morphology in a VR. Abnormally prolonged fragmented and delayed EGMs disappeared (87 ms and 96 ms, light-blue color 1004).

The two examples of ventricular EGMs shown on the right side of FIGS. 10A, 10B and 10C (one above the other) were recorded from the previously abnormal area, and the red asterisks indicate disappearance of the late components. The two EGM panels in each of FIGS. 10A, 10B and 10C are from the CARTO® 3 system and each ECG panel shows V2 ECG lead (top), distal (second from top), proximal bipolar (third from top) and unipolar (bottom) signals at a speed of 200 ms. Of note, in FIG. 10B, V2 lead shows a typical coved-type pattern, which after ablation was modified into a horizontal and flat ST-segment elevation.

FIG. 11 shows a Potential Duration Map and Concentric 'Onion-like' Substrate. This is the same patient as in FIG. 10. The epicardial map shows a concentric 'onion-like' substrate distribution after ajmaline. White lines delimitate multiple areas exhibiting electrograms (EGMs) with different duration (≥300 panel A, ≥250 panel B, and ≥200 ms panel C). Areas with the longest potential duration (≥300 ms) are in the inner circle (panel A), while relatively shorter areas (≥250 and ≥200 ms) are in the outer circle (panels B and C). In FIG. 11, red regions 1101 represent areas with EGM potential duration ≤110 ms. Below each map, there is an example of the EGM recorded in the purple area 1102 (320 ms duration in panel A, 264 in B and 225 in C, respectively). Each EGM panel from the CARTO® system shows V2 ECG lead (top), distal (second from top), proximal bipolar (third from top) and unipolar (bottom) signals at speed of 200 ms speed.

FIG. 12 shows spontaneous type 1 Brugada pattern. The figure refers to a 32-year old patient with spontaneous type 1 Brugada pattern implanted with an ICD due to history of frank syncope without prodromes and an electrophysiological study (EPS) positive for VT/VF induction. In the left panel, the 12-lead ECG with precordial leads placed in V1 and V2 at higher intercostal spaces (II, III and IV ICS) shows typical type 1 Brugada pattern particularly evident in V1 and V2 II ICS and in V1 III ICS. The middle panel of FIG. 12, shows the epicardial PDM in which the purple area 1201 exhibits long duration potentials (≥200 ms; dimensions 21.5 cm2). The two right panels show two examples of electrograms (EGMs) found in the most fragmented and prolonged region (purple area 1201). Of note, typical EGM of wide duration with low voltage and fragmented delayed components are shown in the distal bipolar (second line from top) signal, 320 and 280 ms duration, respectively). In each EGM panel, V1 and V2 II ICS ECG lead (top), distal (second from top), proximal bipolar (third from top) and unipolar (bottom) signals are shown at speed of 200 ms.

Figure 13:
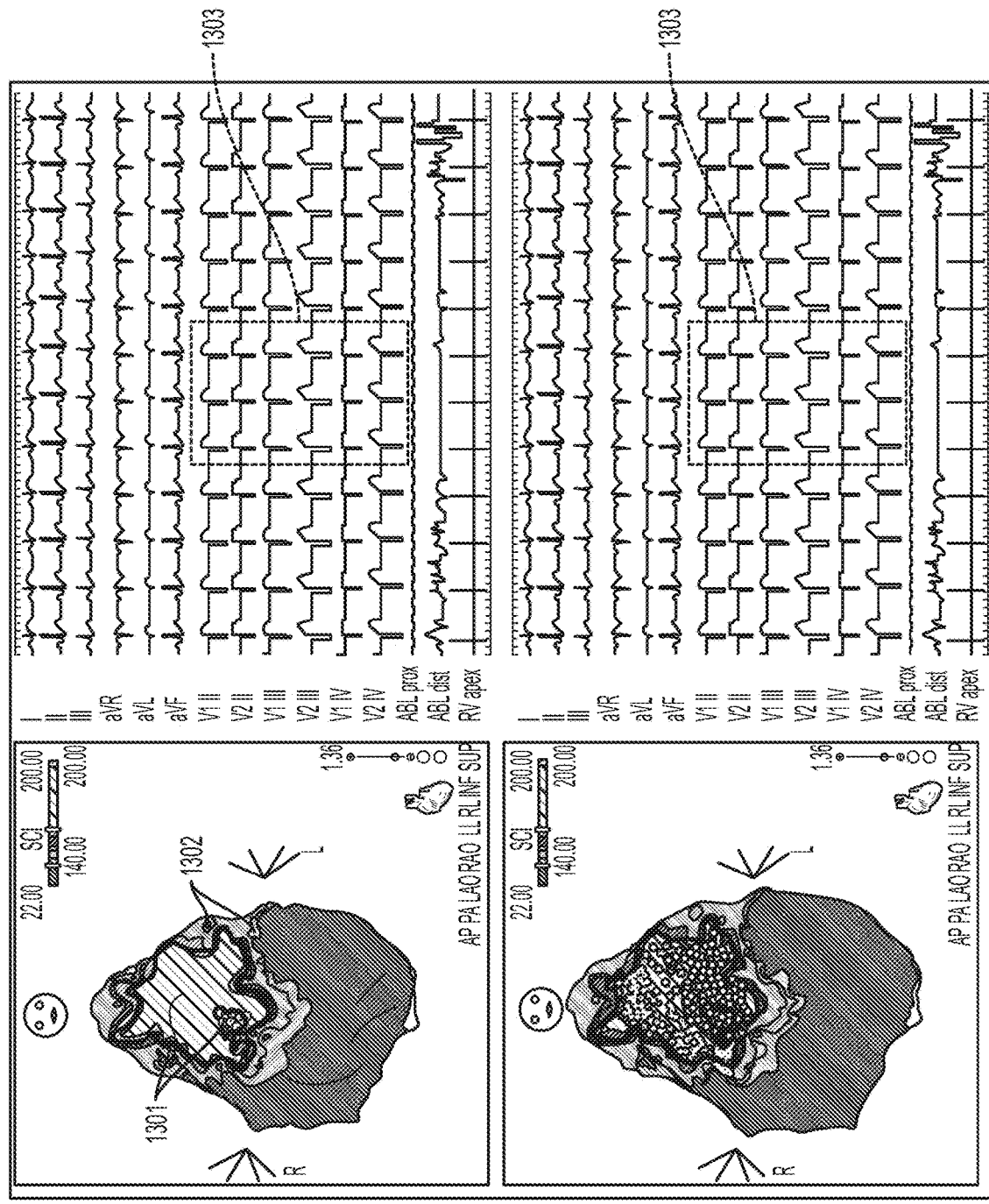
FIG. 13 shows RF ablation in spontaneous type 1 Brugada pattern for one patient.

FIG. 13 shows RF ablation in spontaneous type 1 Brugada pattern, using the same patient as in FIG. 12. The top left panel shows the PDM with white circles 1301 delimitating the areas exhibiting potentials duration ≥300 ms (inner circle) and ≥200 ms (outer circle). RF ablation in the inner circle (red dots 1302) determined initial ascending and horizontal ST-segment elevation in the high right precordial leads, shown in the top panel on the right, box 1303. In the left bottom panel, the complete set of lesions has been delivered in the whole area ≥200 ms resulting in persistent horizontal and flat ST elevation in the right precordial leads, which are not showing the Brugada type 1 pattern at the end of ablation (right bottom panel, red box 1303).

Figure 14:
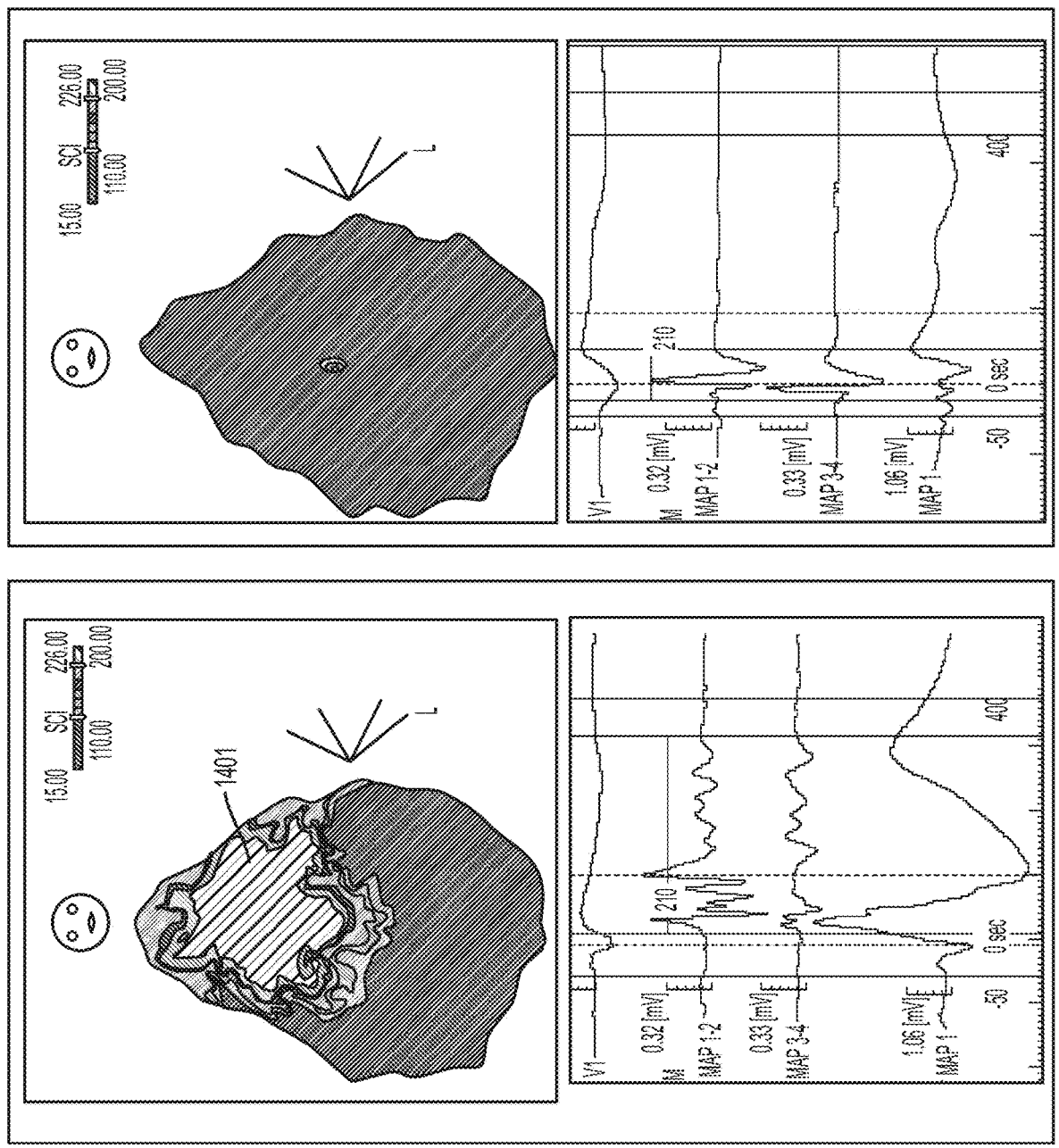
FIG. 14 shows a PDM before and after RF ablation for an example patient.

FIG. 14 shows a PDM before and after RF ablation, using the same patient as in FIG. 12. The left-top panel shows the PDM before ablation. The left-bottom panel shows an example of a wide and fragmented potential discovered in the purple area 1401 (distal bipolar EGM 320 ms duration). After ablation, the PDM in the right-top panel shows the disappearance of abnormally prolonged EGMs, highlighting that the late component has been abolished by ablation (EGM duration 69 ms, right-bottom panel, red asterisk). The EGM showed in the right-bottom panel has been recorded in the same region that had previously exhibited the prolonged and fragmented potential illustrated in the left-bottom panel. The ablation catheter shadow in both CARTO® maps indicates the location where such potentials have been recorded. In each EGM panel, (bottom left and right) V2 II ICS ECG lead (top), distal (second from top), proximal bipolar (third from top) and unipolar (bottom) signals are shown at speed of 200 ms. Of note, in the left-bottom panel, the V2 lead is showing typical coved-type pattern, whereas in the right-bottom panel, the same ECG lead is demonstrating that the Brugada pattern has been modified, showing a horizontal and flat ST segment elevation after ablation.

FIG. 15 shows ECG changes immediately after ablation and thirteen months following the procedure, using the same patient as in FIG. 12. The top panel shows the acute disappearance of the type 1 pattern after RF ablation of the area showing fragmented and prolonged potentials. On the left, the baseline Brugada ECG is followed by the disappearance of the type 1 pattern immediately after ablation (top-middle panel), proved by the final ajmaline challenge repeated at the end of the procedure (top-right panel). The high right precordial leads show horizontal and flat ST-segment elevation that disappears during the follow-up (bottom panel). The bottom panel shows the persistent disappearance of Brugada type 1 pattern, proved by ajmaline challenge thirteen months after ablation. Ajmaline infusion determines PR interval prolongation with QRS broadening and slight ST segment horizontal elevation without the morphological characteristics of the coved-type ECG. From left to right, baseline 12-leads ECG, ECG with high right precordial leads at baseline and after ajmaline administration are shown.

It will be appreciated by persons skilled in the art that the present teachings are not limited to what has been particularly shown and described herein. Instead, the scope of the present teachings include both combinations and sub-combinations of the various features described herein, as well as variations and modifications thereof that are not in the prior art, which would occur to persons skilled in the art upon reading the foregoing description.

What is claimed is:

1. A computer implemented method of identifying target ablation areas in a heart, comprising:
    acquiring electrical signals of the heart over time via a plurality of electrodes disposed at different areas of the heart;
    providing an endocardial duration map for display based on the electrical signals;
    providing an epicardial duration map, comprising at least one or more areas of delimination, for display based on the electrical signals;
    determining when one or more of the areas of delimination have a potential duration greater than a threshold duration amount; and
    identifying the one or more areas of delimination determined as having a potential duration greater than the threshold duration amount as areas to be ablated,
    wherein epicardial ablation is performed on the one or more identified areas of delimination,
    wherein after epicardial ablation is performed on the one or more identified areas of delimination, providing an updated epicardial duration map and determining whether or not a Brugada syndrome (BrS) pattern appears in the updated epicardial duration map, and
    wherein providing the epicardial duration map comprises:
    defining a window of interest (WOI) equal to a time interval comprising at least a heart beat cycle length;
    for each electrical signal:
        calculating heart beats based on the cycle length and a reference annotation;
    assigning each of the heart beats to a sub-WOI within the WOI;
        determining a start potential duration and an end potential duration; and
        selecting an ablation point based on a heart beat having a minimum standard deviation from the heart beats assigned to the sub-WOI.

2. The method according to claim 1, further comprising:
    when it is determined that the BrS pattern appears in the updated epicardial duration map:
        repeating the determining of whether one or more of the areas of delimination have a potential duration greater than the threshold duration amount; and
        repeating the identifying of the one or more areas of delimination determined as having a potential duration greater than the threshold duration amount as the areas to be ablated; and
    when it is determined that the BrS pattern does not appear in the updated epicardial duration map:
        providing a remapped epicardial duration map; and
        determining when one or more areas of delimination in the remapped epicardial duration map are abnormal,
        wherein epicardial ablation is performed on the one or more abnormal areas of delimination.

3. The method according to claim 1,
    wherein the threshold duration amount is 200 ms.

4. The method according to claim 1, further comprising providing an updated epicardial duration map, which maintains an anatomical volume data and adds an electroanatomical data after ajmaline is injected into the heart and prior to determining when the one or more of the areas of delimination have a potential duration greater than a threshold duration amount.

5. The method according to claim 4, further comprising after epicardial ablation is performed on the one or more identified areas of delimination and an additional amount of ajmaline is injected into the heart, providing a new updated epicardial duration map which maintains a new anatomical volume data and adds a new electroanatomical data.

6. The method according to claim 1, wherein the epicardial duration map, and an updated epicardial duration map include displayed concentric areas having cut-off intervals.

7. A system for identifying target ablation areas in a heart, the system comprising:
    a catheter configured to acquire electrical signals acquired over time from different areas of the heart;
    memory configured to store the electrical signals;
    one or more processors configured to:
        provide an endocardial duration map for display based on the electrical signals;
        provide an epicardial duration map, comprising at least one or more areas of delimination, for display based on the electrical signals;
        determine when one or more of the areas of delimination have a potential duration greater than a threshold duration amount;
        identify the one or more areas of delimination determined as having a potential duration greater than the threshold duration amount as areas to be ablated, wherein epicardial ablation is performed on the one or more identified areas of delimination; and
        after epicardial ablation is performed on the one or more identified areas of delimination, provide an updated epicardial duration map and determine whether or not a Brugada syndrome (BrS) pattern appears in the updated epicardial duration map, and
    a display device for displaying the endocardial duration map and the epicardial map,
    wherein the one or more processors are further configured to provide the epicardial duration map by:
    defining a window of interest (WOI) equal to a time interval comprising at least a heart beat cycle length;
    for each electrical signal:
    calculating heart beats based on the cycle length and a reference annotation;
    assigning each of the heart beats to a sub-WOI within the WOI;
    determining a start potential duration and an end potential duration; and selecting an ablation point based on a heart beat having a minimum standard deviation from the heart beats assigned to the sub-WOI.

8. The system according to claim 7, the one or more processors are further configured to:
when it is determined that the BrS pattern appears in the updated epicardial duration map:
repeat the determining of whether one or more of the areas of delimination have a potential duration greater than the threshold duration amount; and
repeat the identifying of the one or more areas of delimination determined as having a potential duration greater than the threshold duration amount as the areas to be ablated; and
when it is determined that the BrS pattern does not appear in the updated epicardial duration map:
provide a remapped epicardial duration map; and
determine when one or more areas of delimination in the remapped epicardial duration map are abnormal,
wherein epicardial ablation is performed on the one or more abnormal areas of delimination.

9. The system according to claim 7, wherein the threshold duration amount is 200 ms.

10. The system according to claim 7, the system further comprising a tool for injecting ajmaline into the heart, and the one or more processors are further configured to provide an updated epicardial duration map, which maintains an anatomical volume data and adds an electroanatomical data after the ajmaline is injected into the heart and prior to determining when the one or more of the areas of delimination have a potential duration greater than a threshold duration amount.

11. The system according to claim 7, wherein the one or more processors are further configured to, after epicardial ablation is performed on the one or more identified areas of delimination and additional ajmaline is injected into the heart, providing a new updated epicardial duration map which maintains an anatomical volume data and adds an electroanatomical data.

12. The system according to claim 7, wherein the one or more processors are further configured to display concentric areas having cut-off intervals on at least one of the epicardial duration map, and an updated epicardial map.

13. A computer software product for identifying target ablation areas in a heart, including a non-transitory computer readable storage medium in which computer program instructions are stored, which instructions, when executed by a computer, cause the computer to:
acquire electrical signals of the heart over time via a plurality of electrodes disposed at different areas of the heart;
provide an endocardial duration map for display based on the electrical signals;
provide an epicardial duration map, comprising at least one or more areas of delimination, for display based on the electrical signals;
determine when one or more of the areas of delimination have a potential duration greater than a threshold duration amount; and
identify the one or more areas of delimination determined as having a potential duration greater than the threshold duration amount as areas to be ablated,
wherein epicardial ablation is performed on the one or more identified areas of delimination,
wherein after epicardial ablation is performed on the one or more identified areas of delimination, provide an updated epicardial duration map and determine whether or not a Brugada syndrome (BrS) pattern appears in the updated epicardial duration map, and
wherein preparing the epicardial duration map comprises:
defining a window of interest (WOI) equal to a time interval comprising at least a heart beat cycle length;
for each electrical signal:
calculating heart beats based on the cycle length and a reference annotation;
assigning each of the heart beats to a sub-WOI within the WOI;
determining a start potential duration and an end potential duration; and
selecting an ablation point based on a heart beat having a minimum standard deviation from the heart beats assigned to the sub-WOI.

14. The computer software product according to claim 13, further comprising:
when it is determined that the BrS pattern appears in the updated epicardial duration map:
repeat the determining of whether one or more of the areas of delimination have a potential duration greater than the threshold duration amount; and
repeat the identifying of the one or more areas of delimination determined as having a potential duration greater than the threshold duration amount as the areas to be ablated; and
when it is determined that the BrS pattern does not appear in the updated epicardial duration map:
provide a remapped epicardial duration map; and
determine when one or more areas of delimination in the remapped epicardial duration map are abnormal,
wherein epicardial ablation is performed on the one or more abnormal areas of delimination.

15. The computer software product according to claim 13, wherein the threshold duration amount is 200 ms.

16. The computer software product according to claim 13, further comprising after epicardial ablation is performed on the one or more identified areas of delimination and additional ajmaline is injected into the heart, providing a new updated epicardial duration map which maintains an anatomical volume data and adds an electroanatomical data.

17. The computer software product according to claim 13, wherein the epicardial duration map, and the updated epicardial duration map include displayed concentric areas having cut-off intervals.

18. A computer implemented method of identifying target ablation areas in a heart, comprising:
acquiring electrical signals of the heart over time via a plurality of electrodes disposed at different areas of the heart;
providing an endocardial duration map for display based on the electrical signals;
providing an epicardial duration map, comprising at least one or more areas of delimination, for display based on the electrical signals;
defining a window of interest (WOI) equal to a time interval comprising at least a heart beat cycle length;
determining when one or more of the areas of delimination have a potential duration greater than a threshold duration amount; and
identifying the one or more areas of delimination determined as having a potential duration greater than the threshold duration amount as areas to be ablated,
wherein epicardial ablation is performed on the one or more identified areas of delimination, and
wherein providing the epicardial duration map comprises:

for each electrical signal:
  calculating heart beats based on the cycle length and a reference annotation;
  assigning each of the heart beats to a sub-WOI within the WOI;
  determining a start potential duration and an end potential duration; and
  selecting an ablation point based on a heart beat having a minimum standard deviation from the heart beats assigned to the sub-WOI.

19. The method according to claim 18, further comprising:
  after epicardial ablation is performed on the one or more identified areas of delimination, providing an updated epicardial duration map and determining whether or not a Brugada syndrome (BrS) pattern appears in the updated epicardial duration map;
  when it is determined that the BrS pattern appears in the updated epicardial duration map:
    repeating the determining of whether one or more of the areas of delimination have a potential duration greater than the threshold duration amount; and
    repeating the identifying of the one or more areas of delimination determined as having a potential duration greater than the threshold duration amount as the areas to be ablated; and
  when it is determined that the BrS pattern does not appear in the updated epicardial duration map:
    providing a remapped epicardial duration map; and
    determining when one or more areas of delimination in the remapped epicardial duration map are abnormal,
    wherein epicardial ablation is performed on the one or more abnormal areas of delimination.

20. The method according to claim 18, wherein the threshold duration amount is 200 ms.

21. The method according to claim 18, further comprising providing an updated epicardial duration map, which maintains an anatomical volume data and adds an electroanatomical data after ajmaline is injected into the heart and prior to determining when the one or more of the areas of delimination have a potential duration greater than a threshold duration amount.

22. The method according to claim 21, further comprising after epicardial ablation is performed on the one or more identified areas of delimination and an additional amount of ajmaline is injected into the heart, providing a new updated epicardial duration map which maintains a new anatomical volume data and adds a new electroanatomical data.

23. The method according to claim 18, wherein the epicardial duration map, and an updated epicardial duration map include displayed concentric areas having cut-off intervals.

24. A system for identifying target ablation areas in a heart, the system comprising:
  a catheter configured to acquire electrical signals acquired over time from different areas of the heart;
  memory configured to store the electrical signals;
  one or more processors configured to:
    provide an endocardial duration map for display based on the electrical signals;
    provide an epicardial duration map, comprising at least one or more areas of delimination, for display based on the electrical signals by defining a window of interest (WOI) equal to a time interval comprising at least a heart beat cycle length;
    determine when one or more of the areas of delimination have a potential duration greater than a threshold duration amount; and
    identify the one or more areas of delimination determined as having a potential duration greater than the threshold duration amount as areas to be ablated,
    wherein epicardial ablation is performed on the one or more identified areas of delimination; and
  a display device for displaying the endocardial duration map and the epicardial map,
  wherein the one or more processors are further configured to provide the epicardial duration map by:
  for each electrical signal:
  calculating heart beats based on the cycle length and a reference annotation;
  assigning each of the heart beats to a sub-WOI within the WOI;
  determining a start potential duration and an end potential duration; and
  selecting an ablation point based on a heart beat having a minimum standard deviation from the heart beats assigned to the sub-WOI.

25. The system according to claim 24, the one or more processors are further configured to:
  after epicardial ablation is performed on the one or more identified areas of delimination, provide an updated epicardial duration map and determine whether or not a Brugada syndrome (BrS) pattern appears in the updated epicardial duration map;
  when it is determined that the BrS pattern appears in the updated epicardial duration map:
    repeat the determining of whether one or more of the areas of delimination have a potential duration greater than the threshold duration amount; and
    repeat the identifying of the one or more areas of delimination determined as having a potential duration greater than the threshold duration amount as the areas to be ablated; and
  when it is determined that the BrS pattern does not appear in the updated epicardial duration map:
    provide a remapped epicardial duration map; and
    determine when one or more areas of delimination in the remapped epicardial duration map are abnormal,
    wherein epicardial ablation is performed on the one or more abnormal areas of delimination.

26. The system according to claim 24, wherein the threshold duration amount is 200 ms.

27. The system according to claim 24, the system further comprising a tool for injecting ajmaline into the heart, and the one or more processors are further configured to provide an updated epicardial duration map, which maintains an anatomical volume data and adds an electroanatomical data after the ajmaline is injected into the heart and prior to determining when the one or more of the areas of delimination have a potential duration greater than a threshold duration amount.

28. The system according to claim 24, wherein the one or more processors are further configured to, after epicardial ablation is performed on the one or more identified areas of delimination and additional ajmaline is injected into the heart, providing a new updated epicardial duration map which maintains an anatomical volume data and adds an electroanatomical data.

29. The system according to claim 24, wherein the one or more processors are further configured to display concentric areas having cut-off intervals on at least one of the epicardial duration map, and an updated epicardial map.

30. A computer software product for identifying target ablation areas in a heart, including a non-transitory computer readable storage medium in which computer program instructions are stored, which instructions, when executed by a computer, cause the computer to:
- acquire electrical signals of the heart over time via a plurality of electrodes disposed at different areas of the heart;
- provide an endocardial duration map for display based on the electrical signals;
- provide an epicardial duration map, comprising at least one or more areas of delimination, for display based on the electrical signals;
- determine when one or more of the areas of delimination have a potential duration greater than a threshold duration amount; and
- identify the one or more areas of delimination determined as having a potential duration greater than the threshold duration amount as areas to be ablated,
- wherein epicardial ablation is performed on the one or more identified areas of delimination,
- wherein preparing the epicardial duration map comprises defining a window of interest (WOI) equal to a time interval comprising at least a heart beat cycle length, and
- wherein preparing the epicardial duration map comprises:
- for each electrical signal:
  - calculating heart beats based on the cycle length and a reference annotation;
  - assigning each of the heart beats to a sub-WOI within the WOI;
  - determining a start potential duration and an end potential duration; and
  - selecting an ablation point based on a heart beat having a minimum standard deviation from the heart beats assigned to the sub-WOI.

31. The computer software product according to claim 30, further comprising:
- after epicardial ablation is performed on the one or more identified areas of delimination, provide an updated epicardial duration map and determine whether or not a Brugada syndrome (BrS) pattern appears in the updated epicardial duration map;
- when it is determined that the BrS pattern appears in the updated epicardial duration map:
  - repeat the determining of whether one or more of the areas of delimination have a potential duration greater than the threshold duration amount; and
  - repeat the identifying of the one or more areas of delimination determined as having a potential duration greater than the threshold duration amount as the areas to be ablated; and
- when it is determined that the BrS pattern does not appear in the updated epicardial duration map:
  - provide a remapped epicardial duration map; and
  - determine when one or more areas of delimination in the remapped epicardial duration map are abnormal,
- wherein epicardial ablation is performed on the one or more abnormal areas of delimination.

32. The computer software product according to claim 30, wherein the threshold duration amount is 200 ms.

33. The computer software product according to claim 30, further comprising after epicardial ablation is performed on the one or more identified areas of delimination and additional ajmaline is injected into the heart, providing a new updated epicardial duration map which maintains an anatomical volume data and adds an electroanatomical data.

34. The computer software product according to claim 30, wherein the epicardial duration map, and the updated epicardial duration map include displayed concentric areas having cut-off intervals.

* * * * *

UNITED STATES PATENT AND TRADEMARK OFFICE
CERTIFICATE OF CORRECTION

PATENT NO. : 11,844,614 B2
APPLICATION NO. : 17/148032
DATED : December 19, 2023
INVENTOR(S) : Carlo Pappone et al.

It is certified that error appears in the above-identified patent and that said Letters Patent is hereby corrected as shown below:

In the Specification

In Column 1, Line 15, delete "2017," and insert -- 2017, now Pat. No. 10,893,819, --, therefor.

In Column 3, Line 27, delete "epicarial" and insert -- epicardial --, therefor.

In Column 4, Line 15, delete "lays" and insert -- lies --, therefor.

In Column 4, Line 19, delete "lays" and insert -- lies --, therefor.

In Column 5, Line 64, delete ">110" and insert -- $\geq$110 --, therefor.

In Column 7, Line 51, delete "(S805=NO)," and insert -- (S705=NO), --, therefor.

In Column 11, Line 65, delete "subxyphoid" and insert -- subxiphoid --, therefor.

In Column 12, Line 10, delete "(imp/" and insert -- (1 mp/ --, therefor.

In Column 14, Line 24, delete "Electrophysiciological" and insert -- Electrophysiological --, therefor.

In Column 16, Line 24, delete "respectively)." and insert -- respectively. --, therefor.

Signed and Sealed this
Twenty-eighth Day of May, 2024

Katherine Kelly Vidal
*Director of the United States Patent and Trademark Office*